United States Patent [19]
Hagishita et al.

[11] Patent Number: 5,776,929
[45] Date of Patent: Jul. 7, 1998

[54] BENZODIAZEPINE DERIVATIVE

[75] Inventors: Sanji Hagishita, Gose; Susumu Kamata, Takarazuka; Kaoru Seno, Nishinomiya; Nobuhiro Haga, Osaka; Yasunobu Ishihara, Kyoto, all of Japan

[73] Assignee: Shionogi & Co., Ltd., Osaka, Japan

[21] Appl. No.: 663,304

[22] PCT Filed: Dec. 19, 1994

[86] PCT No.: PCT/JP94/02132

§ 371 Date: Jun. 25, 1996

§ 102(e) Date: Jun. 25, 1996

[87] PCT Pub. No.: WO95/18110

PCT Pub. Date: Jul. 6, 1995

[30] Foreign Application Priority Data

Dec. 28, 1993 [JP] Japan ................................. 5-336168

[51] Int. Cl.⁶ ...................... A61K 31/55; C07D 243/12
[52] U.S. Cl. ................................ 514/221; 540/518
[58] Field of Search ........................ 540/518; 514/221

[56] References Cited

FOREIGN PATENT DOCUMENTS

| 0 588 104 | 9/1993 | European Pat. Off. ...... C07D 243/12 |
| 558104 | 9/1993 | European Pat. Off. ............. 540/518 |
| 93/14075 | 7/1993 | WIPO ........................... C07D 243/12 |
| 94/24149 | 10/1994 | WIPO ................................ A61K 37/02 |
| 94/24151 | 10/1994 | WIPO ................................ A61K 37/02 |
| 94/25445 | 11/1994 | WIPO ................................ A61K 31/55 |

*Primary Examiner*—Robert T. Bond
*Attorney, Agent, or Firm*—Foley & Lardner

[57] ABSTRACT

A benzodiazepine derivative of the formula (I):

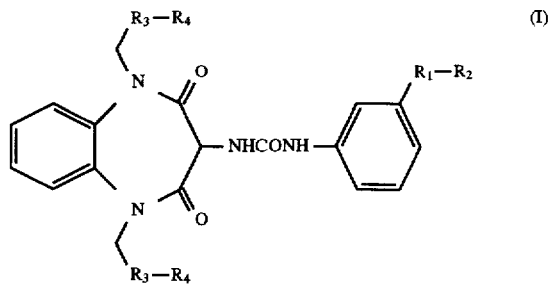

wherein $R_1$ is a bond, $-CH_2-$, $-CH_2O-$, $-SCH_2-$ or a group of the formula:

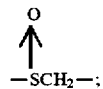

$R_2$ is a lower alkyl, $-COOR_5$, $-CONH(CH_2)_nCOOR_5$, $-CONHSO_2R_5$, $-SO_2NHCOR_5$, or an optionally substituted heterocyclic group ($R_5$ is a hydrogen atom, lower alkyl or benzyl and n is an integer of 1 to 5); $R_3$ is a bond, $-CO-$ or $-CONH-$; and $R_4$ is an optionally substituted heterocyclic group, optionally substituted lower alkyl, optionally substituted lower cycloalkyl, optionally substituted aryl, or lower alkoxycarbonyl group, or a pharmaceutically acceptable salt thereof, which has a high affinity for gastrin receptors and/or CCK-B receptors but not for CCK-A receptors, and is useful for treating diseases associated with gastrin receptors and/or CCK-B receptors without inducing the side effects associated with CCK-A receptors.

5 Claims, No Drawings

BENZODIAZEPINE DERIVATIVE

FIELD OF THE INVENTION

The present invention relates to novel benzodiazepine derivatives capable of competing with gastrin and/or CCK-B and binding to their receptors, and pharmaceutical compositions which contain the same and are useful in the treatment of various diseases associated with gastrin and/or CCK-B receptors.

BACKGROUND OF THE INVENTION

Gastrin and cholecystokinin (CCK) are physiologically active substances belonging to what is called a gastrin sub-family of the gastrointestinal peptide hormone family. Although gastrin receptors are commonly found in various tissues including the whole superior digestive tract, pancreas, liver, biliary duct and the like, they mainly exist on parietal cells of fundic glands and participate in the mediation of gastric acid secretion. As for CCK receptors, it is known that there are two types of receptors, i.e., CCK-A receptor found in peripheral tissues such as digestive gut and CCK-B receptor found in brain. The former participates in the control of gut motility and pancreas secretion whereas the latter in the control of central nervous action, appestat and the like. Accordingly, it has been expected that compounds capable of competing with gastrin and/or CCK-B and binding to their receptors are useful in the treatment of animals including human suffering from gastrointestinal and central nervous diseases associated with receptors for these peptide hormones. For example, such compounds are thought to be useful as an anti-tumor agent; a drug for treating pancreatitis, gallbladder disorder or irritable bowel syndrome, for relieving biliary colic, and for improving appetite. Further, investigations into receptors in both gastrointestinal and central nervous system revealed that these gastrointestinal peptide hormones are also important as biologically active substances ["*Brain and Peptides*" Taisha, vol. 18, No. 10, 33–44 (1981); J. Hughes, C. Woodruff, D. Horwell, A. McKnight & D. Hill, "Gastrin", J. H. Walsh ed., Rovan Press, Ltd., New York, 1993, p. 169–186; F. Makovec, *Drugs of the Future*, 18, 919 (1993); Japanese Patent Publication (KOKAI) 63-238069, EP 167, 919; U.S. Pat. No. 4,820,834; EP 284,256; U.S. Pat. No. 5,004,741].

For instance, gastrin antagonists specific to gastrin receptors are thought to be effective on gastrin-associated disorders such as peptic ulcers in gaster and duodenum, Zollinger-Ellison syndrome, hyperplasia of sinus C cells, and decrease in gastrin activity. The usefulness of antagonists specific to gastrin-receptor in the treatment of gastric and duodenal ulcers has been reported (Taisha, 29/7, 1992, R. Eissele, H. Patberg, H. Koop, W.

Krack, W. Lorenz, A. T. McKnight & R. Arnold, *Gastroenterology*, 103, 1596 (1992), etc.)

There have been reported that antagonists against CCK-B receptor are useful in the reinforcement and elongation of the analgetic effect of opioid-type compounds (e.g., morphine derivatives such as morphine sulfate or hydrochloride) which, are antagonistic against opioid receptors [*Drugs of the future* 18, 919 (1993); *Proc. Natl. Acad. Sci. USA*, Vol. 87, p. 71, 05 September 1990, Neurobiology].

It is necessary to use a compound capable of binding to an intended peptide hormone receptor in preference discriminating it from that for peptide hormones of different subtypes in order to conduct treatment more efficiently.

A series of benzodiazepine derivatives which are antagonistic against gastrin or CCK-B receptor have been disclosed (WO 93/14074 and WO 93/14075). However, they failed to disclose any specific pharmacological data regarding antagonistic activity against gastrin receptors, or antagonists useful as a medicine. Further, all the compounds disclosed in these publications are racemates with an asymmetric carbon atom at the 3-position, which makes the preparation thereof difficult and requires optical resolution to obtain a single compound.

Accordingly, it has been strongly demanded to develop a compound which can bind to an intended receptor discriminating it from other peptide hormone receptor, and is useful as a drug and producible in ease.

DISCLOSURE OF THE INVENTION

In the situations above, the present inventors have studied intensively to develop compounds which have high affinity for gastrin receptors and/or CCK-B receptors with high selectivity but low or no affinity for CCK-A receptors, and found that certain benzodiazepine derivatives are useful for the purposes above and established the present invention.

Thus, the present invention provides a compound of the formula (I):

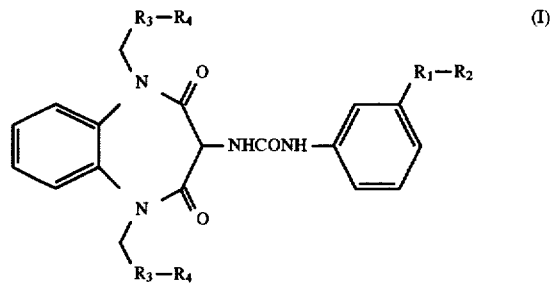

wherein $R_1$ is a bond, $-CH_2-$, $-CH_2O-$, $-OCH_2-$, $-SCH_2-$ or a group of the formula:

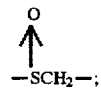

$R_2$ is a lower alkyl, $-COOR_5$, $-CONH(CH_2)_nCOOR_5$, $-CONHSO_2R_5$, $-SO_2NHCOR_5$, or an optionally substituted heterocyclic group ($R_5$ is a hydrogen atom, lower alkyl or benzyl and n is an integer of 1 to 5); $R_3$ is a bond, $-CO-$ or $-CONH-$; and R4 is an optionally substituted heterocyclic group, optionally substituted lower alkyl, optionally substituted lower cycloalkyl, optionally substituted aryl, or lower alkoxycarbonyl group, or a pharmaceutically acceptable salt thereof.

Although all the compounds (I) as defined above are useful to achieve the purposes of the present invention, those of the formula (I) wherein $R_3$ is $-CO-$ and $R_4$ is a lower cycloalkyl group and/or $R_1-R_2$ is $-COOR_5$, $-CONHSO_2R_5$, $-SO_2NHCOR_5$, $-CH_2COOR_5$, $-OCH_2COOR_5$, $-SCH_2COOR_5$, tetrazolylmethyloxy or a 5-membered heterocyclic group containing an N atom are preferable.

THE BEST EMBODIMENT FOR PRACTICING THE INVENTION

Throughout the present specification, the terms "gastrin receptor antagonist" or "CCK-B receptor antagonist" is referred to a compound capable of competitively inhibiting the binding of gastrin receptor or CCK-B receptor with respective natural ligand, and is used interchangeably with the term "gastrin antagonist" or "CCK-B antagonist", respectively. Since the compound (I) of the present invention has a strong affinity for gastrin receptors and/or CCK-B receptors and can bind to them specifically competing with their natural ligands, it may be referred to as "gastrin receptor antagonist" or "CCK-B receptor antagonist".

Because of the same reason above, the terms "gastrin receptor antagonism" and "gastrin antagonism", and the terms "CCK-B receptor antagonism" and "CCK-B antagonism" are used exchangeably.

The following terms used in the definition of compound (I) are defined below.

The term "lower alkyl" means straight or branched chain $C_{1-C8}$ hydrocarbon group including methyl, ethyl, n-propyl, i-propyl, n-butyl, s-butyl, t-butyl, n-pentyl, i-pentyl, neopentyl, s-pentyl, t-pentyl, n-hexyl, neohexyl, i-hexyl, s-hexyl, t-hexyl, heptyl and octyl, and $C_1-C_3$ hydrocarbon group is preferred.

The term "lower cycloalkyl" means $C_3-C_7$ cycloalkyl group including cyclopropyl, cyclobutyl, cyclopentyl, cyclohexyl and cycloheptyl, and $C_3-C_5$ cycloalkyl is preferred.

The term "heterocyclic group" means 5- to 7-membered both aromatic- and non-aromatic heterocyclic groups containing one or more hetero atoms selected independently from the group consisting of O, S and N. Examples of aromatic heterocyclic group include furyl, thienyl, tetrazolyl, pyrrolyl, pyrazolyl, imidazolyl, oxazolyl, thiazolyl, pyridinyl, oxadinyl and triazinyl. Examples of non-aromatic heterocyclic group include pyrrolidinyl, thiazolidinyl, oxazolidinyl, imidazolidinyl, thiazolinyl, oxazolinyl, imidazolinyl, piperidinyl, piperadinyl, morpholinyl, thiomorpholinyl, oxadiazolyl and dioxanyl.

Preferred heterocyclic groups are pyrrolidinyl, thiazolidinyl and thienyl for $R_4$, and tetrazolyl, 5-keto-1,2,4-oxadiazolyl and the like for $R_2$.

The term "aryl" means phenyl, naphthyl and the like.

Examples of substituents in $R_2$ or $R_4$ are hydroxy, carbonyl, amino optionally protected with an amino-protecting group, halogen (F, Cl, Br, etc.), lower alkyl and lower alkoxy.

The term "lower alkoxy" means straight or branched chain $C_1-C_6$ alkoxy group including methoxy, ethoxy, n-propoxy, i-propoxy, n-butoxy, s-butoxy, t-butoxy, n-pentyloxy, i-pentyloxy, neopentyloxy, s-pentyloxy, t-pentyloxy, n-hexyloxy, neohexyloxy, i-hexyloxy, s-hexyloxy and t-hexyloxy, and $C_1-C_3$ alkoxy is preferred.

The benzodiazepine derivatives (I) of the present invention are novel and can be prepared, for example, by alkylating a compound (IV) (3-amino-1H-1,5-benzodiazepine-2,4-(3H,5H)-dione), at the 1- and 5-positions and 3-amino group as described below.

As can be seen from the formula (I), the benzodiazepine derivatives of the present invention have a plane-symmetric structure and are not racemates. This advantageous feature facilitates the preparation of an intended single compound without optical resolution.

The compounds (I) of the present invention can be prepared using any methods known in the art as exemplified below. The following processes are, however, provided for the illustrative purpose only and the scope of the invention should not be limited to compounds (I) prepared according to these processes.

Method 1

A benzodiazepine compound of the formula (IV):

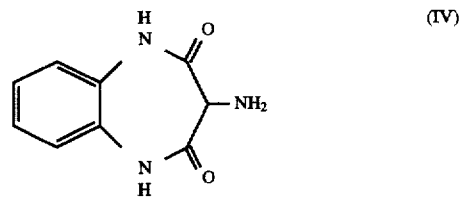

is reacted with a compound of the formula (II):

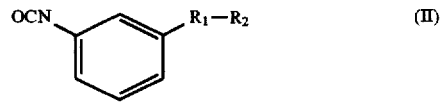

wherein $R_1$ and $R_2$ are as defined above to form a compound of the formula (III) having an urea bond at the 3-position:

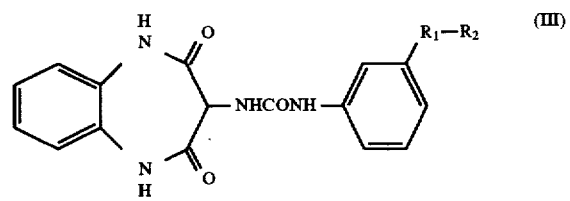

wherein $R_1$ and $R_2$ are as defined above. The compound (III) is then reacted with a compound of the formula (V):

wherein X is a halogen, and $R_3$ and $R_4$ are as defined above for N-alkylation at 1- and 5-positions to give the objective compound (I).

Method 2

An benzodiazepine (IV) is protected at the 3-amino group and N-alkylated by reacting with a compound (V) in a manner similar to that described in Method 1 above, which is followed by deprotection, reaction with a compound (II), and alkylation at the 3-position to give the objective compound (I).

The preparation of compounds (I) of the present invention will be explained in more detail below referring to the method 1. The method 2 can be effected in substantially the same manner except for additional amino-protection and deprotection procedures.

The starting material, i.e., 3-amino-1H-1,5-benzodiazepine-2,4-(3H,5H)-dione (IV), is a known compound and is prepared by any methods described in literatures or those known in the art.

The said compound (IV) is reacted with a compound (II) under the conditions for alkylation, generally in a solvent such as dimethylformamide, methylene chloride or the like at room temperature for about 0.5 to 2 hr.

The N-alkylation of a compound (III) is carried out in general by reacting a compound (III) with a halide of the formula $R_4-R_3—CH_2X$ (V) in the presence of a base such as potassium carbonate or the like and a salt such as potassium iodide or the like in a solvent such as dimethylformamide or the like at room temperature for about 10 to 20 hr. Conventional reagents for N-alkylation such as KOH and $(n-Bu)_4N_4Br^-$, NaH, t-BuOK, $NaNH_2$ and the like are also usable.

A compound of the formula (I) produced by the processes above can be further converted into compounds which are also shown by the formula (I) through the hydrolysis with lithium hydroxide or the like in an alcoholic solvent or the like. The purification of a final product can be carried out in a conventional manner, for example, extracting with an organic solvent such as ethyl acetate, drying, concentrating and/or chromatographing.

A compound of the formula (I) can be optionally converted into a pharmaceutically acceptable salt using an appropriate method known in the art.

The compound (I) of the present invention forms a salt with conventional inorganic or organic acids, or inorganic or organic bases. Examples of salts of the compound (I) include those formed with alkali metals such as sodium, potassium and the like, alkali earth metals such as calcium, magnesium and the like; organic bases such as ammonium, trimethylamine, triethylamine, pyridine, picoline, dicyclohexylamine, N,N'-dibenzylethylenediamine and the like; organic acids such as acetic acid, maleic acid, tartaric acid, methanesulfonic acid, benzenesulfonic acid, formic acid, toluenesulfonic acid, trifluoroacetic acid and the like; inorganic acids such as hydrochloric acid, hydrobromic acid, sulfuric acid, phosphoric acid and the like; and amino acids such as arginine, aspartic acid, glutamic acid and the like.

An intermediate of the formula (III) described above is a novel compound which is useful in the synthesis of not only the compound (I) of the present invention but also various other compounds. The compound (III) can be prepared by any methods known in the art in addition to those described above. For instance, it can be prepared according to the reaction schemes below. All the compounds of the formula (III) are useful as intermediates for the preparation of the compound (I) of the present invention irrespective of the process of preparation.

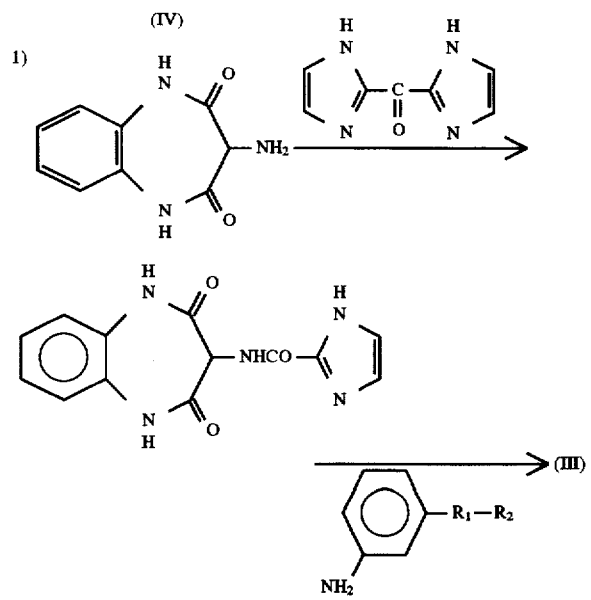

An in vivo experiment (Schild method, Experiment 1 below) revealed that the compound (I) of the present invention can inhibit the gastric acid secretion. As is shown in Experiment 2 below, in vitro experiments have been conducted to examine gastrin- or CCK-B-receptor antagonism of various compounds (I), which revealed that the benzodiazepine derivatives of the present invention have the activities of both types. The experimental results obviously indicate that the benzodiazepine derivatives of the present invention inhibit the gastric acid secretion and are antagonistic against gastrin receptors and/or CCK-B receptors while well discriminating them from CCK-A receptors.

Accordingly, the present invention provides a pharmaceutical composition comprising therapeutically effective amount of a compound (I) in association with pharmaceutically acceptable carriers therefor, which is useful in the treatment of diseases caused by physiological disorders normally controlled through gastrin receptors, for example, gastric ulcer, duodenal ulcer, gastritis, reflux esophagitis and Zollinger-Ellison syndrome, without inducing any side effects associated with CCK-A receptors.

The present invention also provides a pharmaceutical composition comprising therapeutically effective amount of a compound (I) in association with pharmaceutically acceptable carriers therefor, which is useful as an antianxiety drug, or in the treatment of central nervous disorders induced by physiological disorders normally controlled through CCK-B receptors, for example, diseases caused by disorder of appestat-control-system without side effects associated with CCK-A receptors. Further, because the compound (I) seems to be able to enforce or lengthen the analgetic effect induces by opioid-type drugs, it is usable in combination with such analgesics.

The compound (I) of the present invention may be used alone or in combination with one or more other drugs. The combination treatment can be carried out in a manner known in the art by administering a compound (I) and one or more pharmaceutically active ingredients as a single composition, or successively.

The compound (I) of the present invention, when used in combination with an existing drug commonly used as an anti-peptic ulcer agent such as histamine H₂ blocker (H₂B) including cimetidine (Smithkline Beecham), ranitidine (GLAXO), roxatidine (Teikokuzouki), famotidine (Yamanouchi) and the like, or proton-pump inhibitors including omeprazole (Yamanouchi), advantageously exerts the anti-ulcer activity while suppressing the side effects of the co-existing drug through the inherent gastrin inhibitory effect. Thus, one of remarkable drawbacks of H₂B and proton-pump inhibitors is the high incidence of post-treatment relapse following a chronic administration. There are two factors known to be involved in the relapse of ulcer following the H₂B treatment, i.e., (1) rebound phenomenon of acid secretion; and (2) the decrease in the protective function of gastric mucosa. The hypergastrinemia due to chronic administration of a proton-pump inhibitor is also related to the ulcer relapse. The present inventors demonstrated that such reverse effect of H₂B or proton-pump inhibitor could be prevented by administering it in combination with a gastrin receptor antagonist (see, Experiment 4 below). In the Experiment 4, a combined formulation (drug) of a typical H₂B (famotidine), and a known gastrin receptor antagonist (L-365,260 described in Example 281 of Japanese Patent Publication (KOKAI) 63-238069 (EP 167,919; EP 284,256; U.S. Pat. No. 4,820,834; U.S. Pat. No. 5,004,741)) was used to evaluate the inhibitory effect of L-365,260 on the relapse of ulcer following a continuous administration of H₂B on the basis of the appearance of phenomena (1) and (2) above. The result showed that L-365,260 suppressed the appearance of the phenomena (1) and (2) which generally accompanies to the famotidine administration, demonstrating that it is possible to prevent the relapse of ulcer following the anti-ulcer treatment with H₂B. This result indicates that the compound (I) of the present invention having an activity to antagonizing against gastrin receptor should be useful in the prevention of relapse of peptic ulcer after continuous administration of H₂B such as famotidine.

The result obtained in Experiment 4 below also indicates that the compound (I) of the present invention, owing to its activity, inhibits the hypergastrinemia following the continuous administration of proton-pump inhibitors such as omeprazole and the like and is useful in the prevention of relapse of ulcer following the treatment with proton-pump inhibitors. These results indicate that the compound of the present invention is useful in the treatment of refractory ulcers and contribute to solve the problems associated with conventional anti-ulcer agents.

Accordingly, the present invention also provides a pharmaceutical composition for treating ulcers, which comprises a compound (I) of the present invention and an H₂B or a proton-pump inhibitor in association with pharmaceutically acceptable carriers therefor.

Such a composition may contain a compound (I) and an H₂B or proton-pump inhibitor(s) in the ratio of 1–3:3–1, preferably 1:1.

A hybrid-type compound can be prepared by coupling an appropriate H₂B inhibitor to a compound (I) at its R₁–R₂ or R₃–R₄ moiety as shown in Reference Example below.

When using a compound (I) of the present invention in treatment, it can be administered orally or parenterally. In the case of oral administration, a compound of the present invention may be formulated into ordinary formulations in the form of solid such as tablets, powders, granules, capsules and the like; solutions; oily suspensions; liquid formulations such as syrups, elixirs and the like. In the case of parenteral administration, a compound of the present invention may be formulated into an aqueous or oily suspension for injection.

In preparing the formulations, conventional excipients, binders, lubricants, aqueous solvents, oily solvents, emulsifiers, suspending agents or the like may be used. The formulations may contain other additives, such as preservatives, stabilizers or the like.

Although appropriate daily dosage of the compound of the present invention varies depending on the administration route, age, body weight, conditions of the patient, and the kind of disease to be treated, in the case of adult patients, it can generally be between about 10–200 mg, preferably about 20–100 mg on oral administration, and about 1–20 mg, preferably about 2–10 mg on parenteral administration, in 1–2 divisions.

When administering the compound of the present invention as a combined formulation, the dose will be determined on the basis of the dose indicated above.

The following Examples are provided to further illustrate the present invention and are not to be construed as limiting the scope thereof.

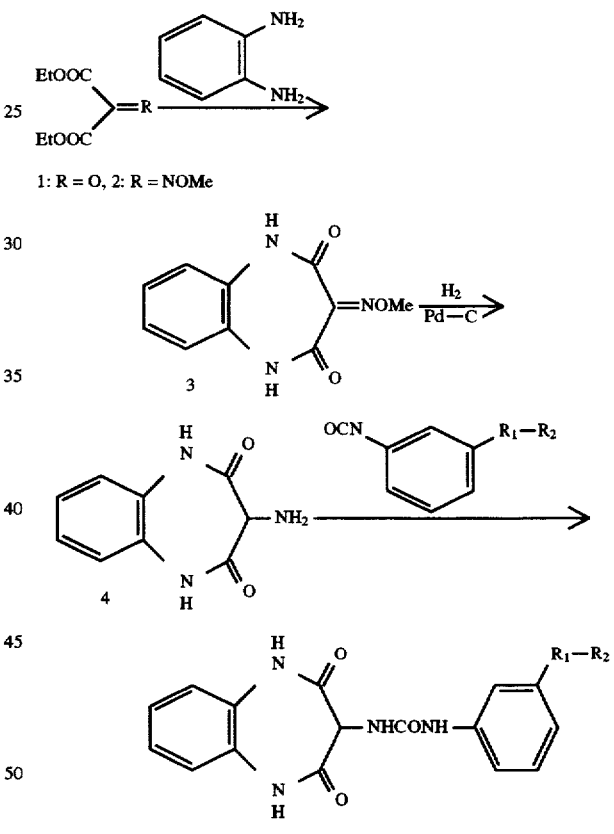

1: R = O, 2: R = NOMe

5: R₁—R₂ = Me
6: R₁—R₂ = CH₂OCONH(CH₂)₃COOMe
7: R₁—R₂ = CH₂OCONH(CH₂)₃COOBn

Preparation 1

Diethyl methoxyiminomalonate 2

A solution of diethyl ketomalonate 1 (51.0 g, 0.293 mmol), o-methylhydroxylamine hydrochloride (24.46 g, 0.293 mmol) and pyridine (23.2 g, 0.293 mmol) in ethanol (250 ml) is heated to reflux for 3 hr. The solvent is removed under reduced pressure. The residue is dissolved in ethyl acetate and washed with water, dilute hydrogen chloride, aqueous sodium hydrogencarbonate solution, and water successively. After drying over sodium sulfate, the solvent is removed under reduced pressure. The resultant residue is distilled under reduced pressure at 80°–85° C./0.5 mmHg to obtain Compound 2 (55.5 g, 93.2%). NNMR (CDCl$_3$)δ: 1.35 (3H, t, J=7.1 Hz), 1.35 (3H, t, J=7.1 Hz), 4.11 (3H, s), 4.36 (2H, q, J=7.1 Hz), 4.37 (2H, q, J=7.1 Hz).

Preparation 2

3-Methoxyimino-1H-1,5-benzodiazepine-2,4(3H,5H)-dione 3

A mixture of iN sodium methylate (162 ml), o-phenylenediamine (17.5 g, 162 mmol) and diethyl 2-(methoxyimino)malonate (32.91 g, 162 mmol) is heated to reflux for 5 hr. After cooling, the mixture is acidified with 2N HCl (162 ml) and pale yellowish crystals (14.3 g, 41%) are filtered off.

IR $v_{max}$ (nujol): 1699, 1655, 1460, 1375 cm$^1$. NMR (CDCl$_3$+CD$_3$OD)δ: 4.03 (3H, s), 7.10–7.28 (4H, m).

Preparation 3

3-Amino-1H-1,5-benzodiazepine-2,4(3H,5H)-dione 4

A solution of 3-methoxyimino-1H-1,5-benzodiazepine-2,4(3H,5H)-dione (3.78 g, 17.4 mmol) and 10% Pd/C (1.8 g) in methanol (300 ml) is stirred for 15 hr under hydrogen gas. After removing the catalyst by filtration, the filtrate is concentrated under reduced pressure. The resultant residue is crystallized from methanol to obtain Compound 4 (2.062 g, 62%). M.p. =290°–291° C.

IR $v_{max}$ (nujol): 3376, 3287, 1704, 1673, 1563 cm$^{-1}$.
NMR (DMSO-d$_6$)δ: 3.75 (1H, s), 7.09–7.25 (4H, m).
Elemental Analysis (for C$_9$H$_9$N$_3$O$_2$·0.1H$_2$O)
Found: C, 56.16; H, 4.88; N, 21.64
Calcd.: C, 56.01; H, 4.80; N, 21.77.

Preparation 4

3-(N'-(m-tolyl)ureido)-1H-1,5-benzodiazepine-2,4(3H,5H)-dione 5

A mixture of 3-amino-1H-1,5-benzodiazepine-2,4(3H,5H)-dione (1.761 g, 9.21 mmol) and m-tolylisocyanate (1.31 g, 10.13 mmol) in dimethylformamide (17 ml) is stirred for 1 hr under ice-cooling. To the reaction mixture is added diisopropyl ether (50 ml) and the resultant crystalline precipitates are filtered off to obtain Compound 5 (2.98 g; yield, 99%). M.p. >300° C.

IR v max (nujol): 3350, 3301, 3215, 3072, 1714, 1656, 1600, 1562 cm$^{-1}$.
NMR (DMSO-d$_6$)δ: 2.23 (3H, s), 4.63 (1H, d, J=7.4 Hz), 6.73 (1H, d, J=7.0Hz), 6.82 (1H, d, J=7.4 Hz), 7.31–7.00 (8H, m), 10.77 (2H, s).
Elemental Analysis (for C$_{17}$H$_{16}$N$_4$O$_3$·0.1H$_2$O)
Found: C, 62.45; H, 5.03; N, 17.13
Calcd.: C, 62.61; H, 5.01; N, 17.18.

Preparation 5

3-(N'-(3-(3-(carbomethoxy)propylcarbamoyloxymethyl)phenyl)ureido)—1H-1,5-benzodiazepine-2,4(3H,5H)-dione 6

A mixture of 3-amino-1H-1,5-benzodiazepine-2,4(3H, 5H)-dione (1.91 g, 10.0 mmol) and 3-(3-(carbomethoxy)propylcarbamoyloxymethyl)phenylisocyanate (3.507 g, 12.0 mmol) in dimethylformamide (19 ml) is stirred for 1 hr at room temperature. To the residue obtained by concentrating the reaction mixture under reduced pressure is added methylene chloride (300 ml) and methanol (100 ml), and the mixture is stirred for 30 min at room temperature. The reaction mixture is filtered through a silica gel (50 g) layer to obtain Compound 6 (4.822 g, 100%) as colorless crude crystals. M.p. =151°–155° C.

IR $v_{max}$ (nujol): 3273, 1722, 1698, 1636, 1599, 1567, 1529, 1502cm$^{-1}$.
NMR (DMSO-d$_6$)δ: 1.64 (2H, qui, J=7.0 Hz), 2.30 (2H, t, J=7.4 Hz), 3.00 (2H, q, J=5.8 Hz), 3.57 (3H, s), 4.64 (1H, d, J=7.4 Hz), 4.93 (2H,s), 6.79–6.92 (2H, m), 7.12–7.40 (8H, m), 9.18 (1H, s), 10.78 (2H,s).

Preparation 6

3-(N'-(3-(3-(benzyloxycarbonyl)propylcarbamoyloxymethyl)phenyl)ureido)-1H-1,5-benzodiazepine-2,4(3H,5H)-dione 7

Compound 7 is prepared in a manner similar to that used for preparation of Compound 6 above. M.p. =233°–235° C.

IR $v_{max}$ (KBr): 3386, 3287, 1716, 1697, 1636, 1599, 1566 cm$^{-1}$.
NMR (DMSO-d$_6$1)δ: 1.67 (2H, qui, J=7.2 Hz), 2.37 (2H, t, J=7.4 Hz), 3.01 (2H, q, J=6.2 Hz), 4.64 (1H, d, J=7.6 Hz), 4.93 (2H, s), 5.07 (2H, s), 6.86 (2H, dd, J=5.7, 7.1 Hz), 7.14–7.40 (8H, m), 7.36 (5H, s), 9.18 (1H, s), 10.77 (2H, S).
Elemental Analysis (for C$_{29}$H$_{29}$N$_5$O$_7$·0.5H$_2$O)
Found: C, 61.32; H, 5.37; N, 12.55
Calcd.: C, 61.26; H, 5.32; N, 12.32.

Preparation 7

Chloromethyl cyclopentyl ketone

To cyclopentanecarboxylic acid (5.71 g, 5 mmol) is added thionyl chloride (11.9 g, 10 mmol) and the mixture is stirred for 2 hr at room temperature. After removing excessive thionyl chloride under reduced pressure, the mixture is distilled at 48–52/18 mmHg to obtain acid chloride (5.54 g, 83.5%). A solution of the acid chloride (5.54 g) in ether (5 ml) is added dropwise to a solution of excessive diazomethane in ether under ice-cooling. The mixture is stirred for 30 min and concentrated under reduced pressure to about half of its original volume. The solution is added dropwise to conc. HCl at −20° C. and the mixture is stirred for 3 hr. After adding ice-cold water, the organic layer is separated, washed with water and dried over sodium sulfate. The solvent is removed under reduced pressure and the residue is distilled at 88–92/18 mmHg to obtain the objective compound (3.53 g, 58.4%).

NMR (CDCl$_3$)δ: 1.5–2.0 (8H, m), 3.12 (1H, m), 4.17 (2H, s).

In a manner similar to that described above, 2-(chloroacethyl)furan, 2-(chloroacethyl)thiophene, 4-(chloroacetyl)-1,2-dimethoxybenzene, chloroacetylcyclopropane, and o-methylphenacyl chloride were prepared.

Preparation 8

Bromoacetylpyrrolidine

A solution of pyrrolidine (3.97 g, 55 mmol) and triethylamine (5.84 g, 57.7 mmol) in methylene chloride (25 ml) is added dropwise to a solution of bromoacetyl bromide (11.28 g, 91.7 mmol) in methylene chloride (25 ml) under ice-cooling. The mixture is stirred at 0° C. for 30 min then at room temperature for 30 min, and poured into ice-cold water. The organic layer is separated, washed with water, dried over sodium sulfate and concentrated under reduced pressure.

In a manner similar to that described above, bromoacetylthiazolidine, cyclopropylchloroacetamide were prepared.

Preparation 9

3-(t-Butoxycarbonylamino)-1H-1,5-benzodiazepine-2,4(3H,5H)-dione 13

To a suspension of 3-amino-1H-1,5-benzodiazepine-2,4(3H,5H)-dione 4 (3.27 g, 17.1 mmol) in tetrahydrofuran (300 ml) is added di-tert-butyl dicarbonate (5.62 g, 25.8 mmol). The mixture is stirred for 24 hr at room temperature and concentrated. To the residue is added a mixture (200 ml) of methylene chloride/methanol (9:1) and water (50 ml) and the mixture is stirred for 10 min. The organic layer is dried over magnesium sulfate and concentrated under reduced pressure. Crystallization from a mixture of methylene chloride/methanol and diisopropyl ether yields the titled Compound 13 (4.5 g, Yield 90%) as white crystals. M.p. =243°–244° C.

NMR (DMSO-d$_6$)δ: 1.38 (9H, m), 4.51 (1H, d, J=8.2 Hz), 6.48 (1H, d, J=8.2 Hz), 7.14–7.31 (4H, m), 10.54–10.93 (2H, broad).

Elemental Analysis (for $C_{14}H_{17}N_3O_4$)

Calcd.: C, 57.72; H, 5.88; N, 14.43

Found: C, 57.45; H, 5.88; N, 14.36.

Preparation 10

1,5-Bis-(cyclopropylcarbonylmethyl)-3-(t-butoxycarbonylamino)-1H-1,5-benzodiazepine-2,4 (3H,5H)-dione 14 h A suspension of 3-(t-butoxycarbonylamino)-1H-1,5-benzodiazepine-2,4(3H,5H)-dione 13 (2.039 g, 7 mmol), cyclopropylcarbonylmethyl chloride (2.488 g, 21 mmol), potassium carbonate (2.902 g, 21 mmol) and potassium iodide (174 mg, 1.05 mmol) in dimethylformamide (20 ml)

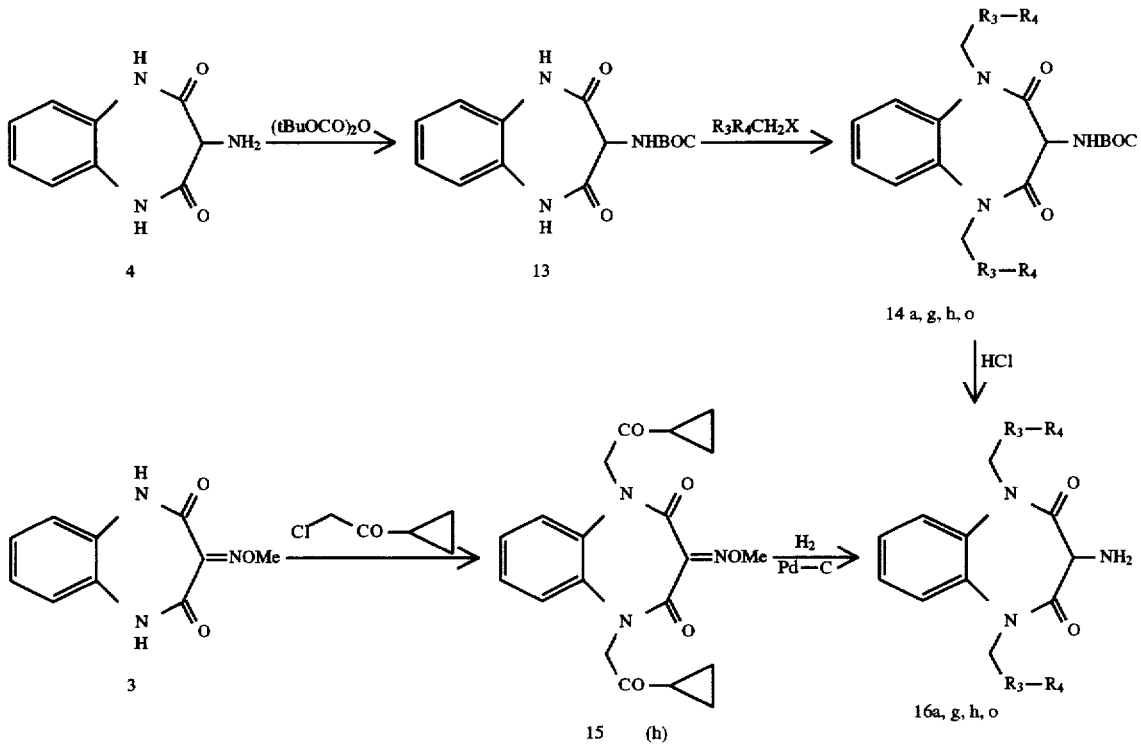

is stirred for 15 hr at room temperature. The reaction mixture is concentrated under reduced pressure. Purification of the residue by column chromatography on silica gel (toluene:ethyl acetate, 2:1) gives the titled Compound 14 h (3.188 g; yield, 100%) as a foam.

IR $v_{max}$ (KBr): 3445, 1700, 1658, 1503, 1450, 1320 cm$^{-1}$.

NMR (DMSO-d$_6$)δ: 0.81–1.06 (8H, m) 1.35 (9H, s), 2.05–2.22 (2H, m), 4.82 (2H, d, J=18.4 Hz), 4.85 (1H, d, J=8.2 Hz), 4.96 (2H, d, J=18.4 Hz), 6.73 (1H, d, J=8.2 Hz), 7.27–7.45 (4H, m).

Elemental Analysis (for $C_{24}H_{29}N_3O_6 \cdot 0.2H_2O$)

Calcd.: C, 62.79; H, 6.45; N, 9.15

Found: C, 62.92; H, 6.44; N, 8.94.

Preparation 11

1,5-Bis-(pyrrolidinocarbonylmethyl)-3-(t-butoxycarbonylamino)-1H-1,5-benzodiazepine-2,4 (3H,5H)-dione 14a Compound 14a is prepared in a manner similar to that used for preparation of Compound 14 h using previously prepared Compound 13 and pyrrolidinocarbonylmethyl bromide.

M.p. =137°–139° C.

13

IR $v_{max}$ (KBr): 3440, 1700, 1503, 1420 cm$^{-1}$.

NMR (DMSO-d$_6$)δ: 1.36 (9H, s), 1.65–1.96 (8H, m), 3.23–3.38 (4H, m), 3.39–3.52 (4H, m), 4.47 (2H, d, J=16.6 Hz), 4.68 (2H, d, J=16.6 Hz), 4.83 (1H, d, J=8.2 Hz), 6.57 (1H, d, J=8.2 Hz), 7.32–7.46 (2H, m), 7.47–7.57 (2H, m).

Elemental Analysis (for C$_{26}$H$_{35}$N$_5$O$_6$·0.7H$_2$O)

Calcd.: C, 59.35; H, 6.97; N, 13.31

Found: C, 59.35; H, 6.84; N, 13.14.

Preparation 12

1,5-Bis-(thienylcarbonylmethyl)-3-(t-butoxycarbonylamino)-1H-1,5-benzodiazepine-2,4(3H,5H)-dione 14g Compound 14g is prepared in a manner similar to that used for preparation of Compound 14 h using previously prepared Compound 13 and 2-thienylcarbonylmethyl chloride.

M.p. =132°–135° C.

IR $v_{max}$ (KBr): 3435, 1703, 1672, 1503, 1419 cm$^{-1}$.

NMR (DMSO-d$_6$)δ: 1.36 (9H, s), 4.96 (1H, d, J=8.4 Hz), 5.27 (2H, d, J=18.0Hz), 5.52 (2H, d, J=18.0 Hz), 6.82 (1H, d, J=8.4 Hz), 7.28–7.36 (2H, m), 7.45 (4H, d, J=2.0Hz), 8.10–8.18 (4H, m).

Elemental Analysis (for C$_{26}$H$_{25}$N$_3$O$_6$S$_2$·0.2H$_2$O)

Calcd.: C, 57.49; H, 4.71; N, 7.74; S, 11.80

Found: C, 57.54; H, 4.81; N, 7.71; S, 11.69.

Preparation 13

1,5-Bis-(cyclopropylmethyl)-3-(t-butoxycarbonylamino)-1H-1,5-benzodiazepine-2,4(3H,5H)-dione 14o Compound 14o is prepared in a manner similar to that used for preparation of Compound 14 h using previously prepared Compound 13 and cyclopropylmethyl chloride.

M.p. =156°–157° C.

IR $v_{max}$ (KBr): 3430, 3370, 1695, 1500, 1419 cm$^{-1}$.

NMR (DMSO-d$_6$) δ: 0.04–0.17 (4H, m), 0.21–0.36 (4H, m), 0.69–0.89 (2H, m), 1.35 (9H, s), 3.64 (2H, dd, J=14.6 & 6.8 Hz), 4.14 (2H, dd, J=14.6 & 6.8 Hz), 4.65 (1H, d, J=8.2 Hz), 6.45 (1H, d, J=8.2 Hz), 7.37–7.49 (2H, m), 7.63–7.77 (2H, m).

Elemental Analysis (for C$_{26}$H$_{35}$N$_5$O$_6$)

Calcd.: C, 59.35; H, 6.97; N, 13.31

Found: C, 59.35; H, 6.84; N, 13.14.

Preparation 14

1,5-Bis-(cyclopropylmethyl)-3-(methoxyimino)-1H-1,5-benzodiazepine-2,4(3H,5H)-dione 15

Compound 15 is prepared in a manner similar to that described in Example 1 below for preparation of Compound 8a in 87.1% yield.

M.p. =228°–230° C.

IR $v_{max}$(KBr): 3443, 1714, 1678, 1660, 1598, 1503 cm$^{-1}$.

NMR (CDCl$_3$)δ: 0.93–1.08 (4H, m),1.15 (4H, m), 2.03 (2H, m), 3.96 (3H, s), 4.78 (2H, d, J=17.6 Hz), 4.90 (1H, d, J=17.6 Hz), 4.92 (2H, d, J=17.6 Hz), 7.17–7.33 (4H, m).

Elemental Analysis (for C$_{20}$H$_{21}$N$_3$O$_5$)

Calcd.: C, 62.65; H, 5.52; N, 10.96

Found: C, 62.41; H, 5.62; N, 11.02.

Preparation 15

1,5-Bis-(cyclopropylcarbonylmethyl)-3-amino-1H-1,5-benzodiazepine-2,4(3H,5H)-dione 16 h 1) To a solution of previously prepared 1,5-bis-(cyclopropylcarbonylmethyl)-3-(t-butoxycarbonylamino)-1H-1,5-benzodiazepine-2,4(3H,5H)-dione 14 h (3.188 g) in ethyl acetate (16 ml) is added a solution of 4N HCl in ethyl acetate (14 ml) under ice-cooling. After stirring the reaction mixture for 15 hr at room temperature, crystalline preparations are filtered off. The resultant crystals are dissolved into methylene chloride/methanol (5:1) and washed with saturated aqueous sodium hydrogencarbonate solution. The organic layer is dried over magnesium sulfate and concentrated under reduced pressure. Crystallization from a mixture of methylene chloride, methanol and diisopropyl ether yields the titled Compound 16 h (2.092 g; yield, 84%).

M.p. =237°–238° C.

IR $v_{max}$(KBr): 3375, 1700, 1667, 1600, 1505, 1416, 1389 cm$^{-1}$.

NMR (DMSO-d$_6$)δ: 0.79–1.03 (8H, m), 1.82–2.00 (2H, brs), 2.05–2.21 (2H, m), 4.08 (1H, s), 4.74(2H, d, J=18.2 Hz), 4.96 (2H, d, J=18.2 Hz), 7.19–7.30 (2H, m), 7.30–7.40(2H, m).

Elemental Analysis (for C$_{19}$H$_{21}$N$_3$O$_{4}$·0.3H$_2$O)

Calcd.: C, 63.25; H, 6.03; N, 11.65

Found: C, 63.35; H, 5.92; N, 11.65.

2) To a suspension of Compound 14 (3.34 g, 8.71 mmol) in methanol (320 ml) is added 10% Pd/C (1.5 g) and the mixture is stirred for 20 hr under hydrogen gas. Organic substances are dissolved by the addition of chloroform and the catalysts are filtered off. The residue obtained by distilling the solvent under reduced pressure is dissolved into chloroform (100 ml) and methanol (300 ml), and again subjected to the reduction with 10% Pd/C catalyst for 20 hr. After removing the catalysts by filtration, the solvent is distilled under reduced pressure and the residue is re-precipitated from methanol-ethyl acetate to obtain Compound 16 h (3.05 g, 98.5%).

Preparation 16

1,5-Bis-(pyrrolidinocarbonylmethyl)-3-amino-1H-1,5-benzodiazepine-2,4(3H,5H)-dione 16a Compound 16a is prepared by treating the previously obtained Compound 14a in a manner similar to that described in Preparation 15 for the preparation of Compound 16 h.

M.p. =246°–247° C.

IR $v_{max}$(KBr): 3445, 1700, 1655, 1500, 1450, 1320 cm$^{-1}$.

NMR (DMSO-d$_6$)δ: 1.63–2.00 (10H, m), 3.23–3.38 (4H, m), 3.40–3.53 (4H, m), 4.04 (1H, s), 4.39(2H, d, J=16.6 Hz), 4.69 (2H, d, J=16.6 Hz), 7.29–7.40 (2H, m), 7.40–7.51(2H, m).

Elemental Analysis (for C$_{21}$H$_{27}$N$_5$O$_4$·0.7H$_2$O)

Calcd.: C, 59.20; H, 6.72; N, 16.44

Found: C, 59.38; H, 6.46; N, 16.20.

Preparation 17

1,5-Bis-(thienylcarbonylmethyl)-3-amino-1H-1,5-benzodiazepine-2,4(3H,5H)-dione 16g Compound 16g is prepared by treating the previously obtained Compound 14g in a manner similar to that described in Preparation 15, 1).

M.p. =208–209° C.

IR $v_{max}$ (KBr): 3450, 1700, 1679, 1662, 1585, 1502, 1419, 1241 cm$^{-1}$.

NMR (DMSO-d$_6$) δ: 1.96 (2H, s), 4.21 (1H, s), 5.18 (2H, d, J=18.0Hz), 5.51 (2H, d, J=18.0Hz), 7.26–7.45 (6H, m), 8.08–8.20 (4H, m).

Elemental Analysis (for $C_{21}H_{17}N_3O_4S_2$)

Calcd.: C, 57.39; H, 3.90; N, 9.56; S, 14.59

Found: C, 57.28; H, 4.03; N, 9.40; S, 14.40.

Preparation 18

1,5-Bis-(cyclopropylmethyl)-3-amino-1H-1,5-benzodiazepine-2,4(3H,5H)-dione 16o

Compound 16o is prepared by treating the previously obtained Compound 14o in a manner similar to that described in Preparation 15, 1).

M.p. =147°–148° C.

IR $v_{max}$ (KBr): 3380, 1696, 1660, 1600, 1500, 1422 cm$^{-1}$.

NMR (DMSO-d$_6$)δ: 0.04–0.17 (4H, m), 0.22–0.35 (4H, m), 0.70–0.90 (2H, m), 1.89 (2H, br.s), 3.63 (2H, dd, J=14.2 & 6.6 Hz), 3.89 (1H, s), 4.12 (2H, dd, J=14.2 & 6.6 Hz), 7.32–7.43 (2H, m), 7.58–7.71 (2H, m).

Elemental Analysis (for $C_{17}H_{21}N_3O_2$)

Calcd.: C, 68.21; H, 7.07; N, 14.04

Found: C, 68.20; H, 7.12; N, 13.96.

Preparation 19

Ethyl 3-(N-BOC-amino)phenylthioacetate

To a solution of m-aminobenzenethiol (2.0 g, 15.9 mmol) in acetone (20 ml) are added di-t-butyl dicarbonate (3.50 g, 16.04 mmol), then 5% aqueous sodium hydrogencarbonate solution (10 ml) under ice-cooling. The mixture is stirred at 0° C. for 30 min followed by at room temperature for 15 hr. After addition of ethyl acetate, the reaction mixture is washed with water, dried over sodium sulfate and distilled under reduced pressure to remove the solvent. The resultant residue is purified by column chromatography on silica gel (100 g silica gel; and hexane/toluene, 2:1) to obtain a product (3.09 g, 85.8%). To a solution of the resultant compound (3.09 g) in acetone (50 ml) is added potassium carbonate (10 g). To the mixture is added dropwise ethyl bromoacetate (2.35 g) with stirring. After the reaction mixture is stirred for 3 days, ether is added thereto and insoluble substances are removed by filtration and the filtrate is distilled under reduced pressure. The resultant residue is purified by column chromatography (100 g silica gel; and hexane/ethyl acetate, 3:1 to 2:1) and crystallization from ether/hexane to give the titled objective compound (2.4 g, 56.2%).

M.p. =70°–71° C.

IR$v_{max}$ (KBr): 3424, 3353, 1717, 1599, 1538 cm$^{-1}$.

NMR (CDCl$_3$) δ: 1.24 (3H, t, J=7.3 Hz), 1.51 (9H, s), 3.64 (2H, s), 4.18 (2H, q, J=7.3 Hz), 6.50 (1H, s), 7.00–7.11 (1H, m), 7.15–7.25 (2H, m), 7.47 (1H, m).

Elemental Analysis (for $C_{15}H_{28}NO_4S$)

Calcd.: C, 57.86; H, 6.80; N, 4.50; S, 10.30

Found: C, 57.61; H, 6.82; N, 4.67; S, 10.27.

Preparation 20

Ethyl 3-aminophenylthioacetate

A solution (4 ml) of 4N-hydrogen chloride in ethyl acetate is added to a solution of the above-mentioned BOC compound (1.255 g) in ethyl acetate (4 ml) and the mixture is stirred for 3 hr at room temperature. After the addition of 5% sodium hydrogencarbonate (20 ml), the reaction mixture is extracted with ethyl acetate. The extract is washed with water, dried over sodium sulfate and distilled to remove the solvent. The resultant crude amine (846 mg) is used in the next step without further purification.

NMR (CDCl$_3$)δ: 1.24 (3H, t, J=7.1 Hz), 3.62 (2H, s), 4.18 (2H, q, J=7.1 Hz), 6.54 (1H, ddd, J=1.0, 2.3, 8.0 Hz), 6.72–6.81 (2H, m), 7.08 (1H, t, J=7.7 Hz).

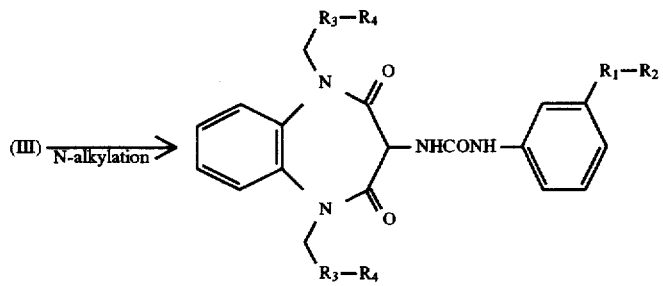

8a, d–f, h, k–t, u: R$_1$—R$_2$= Me 9a, b, d, f–i, n, o, t, u: R$_1$—R$_2$= —CH$_2$OCONH(CH$_2$)$_3$COOMe 10c, i, k, s, t, u: R$_1$—R$_2$= —CH$_2$OCONH(CH$_2$)$_3$COOBn ⎤ hydrolysis 11a, c, d, f, g, n, o: R$_1$—R$_2$= —CH$_2$OCONH(CH$_2$)$_3$COOH ⎦

R$_3$—R$_4$ =

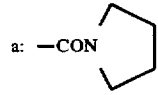
a: —CON⟩

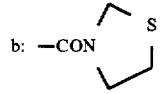
b: —CON⟩S

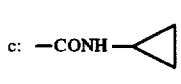
c: —CONH—◁

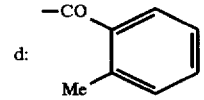
d: —CO-⟨Me⟩

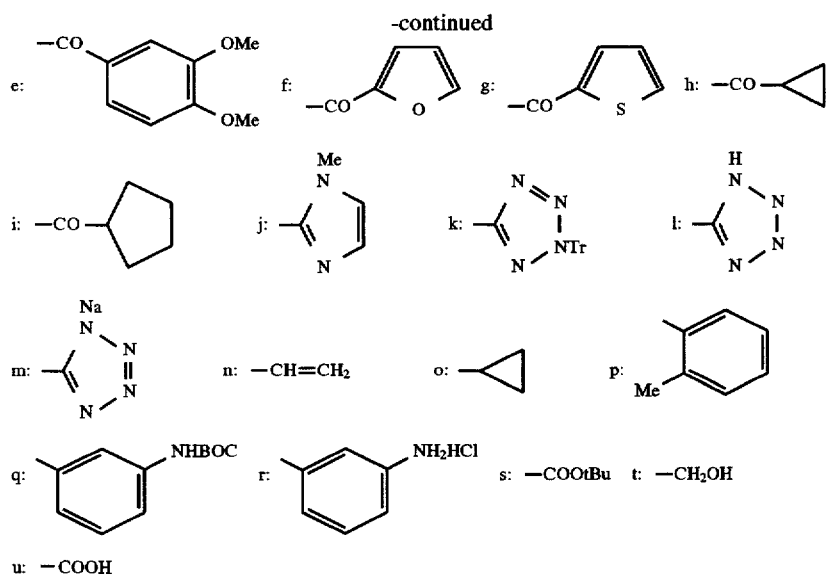

EXAMPLE 1

1,5-Bis-(pyrrolidinocarbonylmethyl)-3-(N'-m-tolyl)ureido)-1H-1,5-benzodiazepine-2,4(3H,5H)-dione
8a The objective Compound 8a was prepared by N-alkylating a compound prepared in Preparation 4, 5 or 6 in accordance with the general procedures described below.

Thus, a mixture of Compound 5, 6 or 7 (1.06 mmol) prepared in Preparation 4, 5 or 6 above and either of halides (2.40 mmol) prepared in Preparation 7 and 8, potassium carbonate (553 mg, 4.00 mmol) and potassium iodide (80 mg, 0.48 mmol) in dimethylformamide is stirred for 15 hr. The reaction mixture is poured into ice-cold water and extracted with ethyl acetate. The extract is washed with water, dried over sodium sulfate and distilled under reduced pressure to remove the solvent. The residue is purified by column chromatography on silica gel (100 g gel; and chloroform/methanol).

IR $v_{max}$ (KBr): 3421, 1694, 1655, 1557 cm$^{-1}$.

NMR (CDCl$_3$) δ: 1.70–2.05 (8H, m), 2.25 (3H, s), 3.47 (8H, m), 4.60 (4H, s), 5.23 (1H, m), 6.33 (1H, m), 6.79 (1H, m), 7.04–7.15 (3H, m), 7.22 (1H, s), 7.28 (2H, m), 7.51 (2H, m).

Elemental Analysis (for C$_{29}$H$_{34}$N$_6$O$_5$·0.6H$_2$O)
Calcd: C, 62.41; H, 6.42; N, 15.04
Found: C, 62.49; H, 6.36; N, 15.08.

Compounds 8d, 8e, 8f, 8h, 8k, and 8l described in the following Examples were prepared in a manner similar to that described in Example 1 from corresponding starting materials.

EXAMPLE 2

1,5-Bis-(o-methylphenacyl)-3-{N'-(m-tolyl)-ureido}-1H-1,5-benzodiazepine-2,4(3H,5H)-dione 8d M.p. =239°–242° C.

IR $v_{max}$ (KBr): 3408, 3363, 1691, 1670, 1643, 1614, 1600, 1571, 1501 cm$^{-1}$.

NMR (CDCl$_3$+CD$_3$OD)δ: 2.29 (3H, s), 2.41 (6H, s), 5.07 (4H, s), 5.39 (1H, s), 6.80 (1H, m), 7.14 (2H, m), 7.22–7.39 (9H, m), 7.45 (2H, m), 7.65(2H, d, J=7.4 Hz).

Elemental Analysis (for C$_{35}$H$_{32}$N$_4$O$_5$·0.5H$_2$O)
Found: C, 70.28; H, 5.43; N, 9.52
Calcd.: C, 70.34; H, 5.57; N, 9.37.

EXAMPLE 3

1,5-Bis-(3,4-dimethoxyphenacyl)-3-(N'-(m-tolyl)-ureido)-1H-1,5-benzodiazepine-2,4(3H,5H)-dione
8e Yield, quantitative; m.p. =266°–268° C.

IR $v_{max}$ (KBr): 3355, 1699, 1678, 1665, 1649, 1614, 1596, 1568 cm$^{-1}$.

NMR (DMSO+CD$_3$OD)δ: 2.24 (3H,s), 3.85 (6H,s), 3.89 (6H,s), 5.15 (1H,d, (2 Hz), 5.29 (2H, d, J=18.0Hz), 5.55 (2H, d, J=18.0 Hz), 6.73 (1H, d, J=5.8 Hz), 6.89 (1H, d, J=8.2 Hz), 7.04–7.16 (4H, m), 7.20 (1H,s), 7.41 (4H, s), 7.52 (2H, d, J=2.0 Hz), 7.74 (2H, dd, J=2.8, 8.2 Hz), 9.04 (1H, s).

Elemental Analysis (for C$_{37}$H$_{36}$N$_4$O$_9$·0.4H$_2$O)
Found: C, 64.60; H, 5.53; N, 8.10
Calcd.: C, 64.60; H, 5.39; N, 8.14.

EXAMPLE 4

1,5-Bis-(2-furylcarbonylmethyl)-3-{N'-(m-tolyl)-ureido}-1H-1,5-benzodiazepine-2,4(3H,5H)-dione
8f M.p. =296°–298° C. (decomposition).

IR $v_{max}$ (nujol): 3367, 1706, 1689, 1663, 1644, 1570 cm$^{-1}$.

NMR (DMSO-d$_6$) δ: 2.22 (3H, s), 5.10 (1H, d, J=8.2 Hz), 5.12 (2H, d, J=18.0Hz), 5.38 (2H, d, J=18.0Hz), 6.73 (1H, s), 6.80 (2H, dd, J=3.6 & 1.6 Hz), 7.10 (2H, d, J=4.4 Hz), 7.19 (1H, s), 7.37–7.55 (4H, m), 7.64 (2H, d, J=3.6 Hz), 8.10 (2H, d, J=1.6 Hz), 9.05 (1H, s).

Elemental Analysis (for C$_{29}$H$_{24}$N$_4$O$_7$·0.5H$_2$O)
Found: C, 63.28; H, 4.57; N, 10.32
Calcd.: C, 63.38; H, 4.59; N, 10.20.

EXAMPLE 5

1,5-Bis-(cyclopropylcarbonylmethyl)-3-(N'-(m-tolyl)ureido)-1H-1,5-benzodiazepine-2,4(3H,5H)-dione 8h Yield, 74%; m.p. =246°–248° C.

IR $v_{max}$(KBr): 3380, 1700, 1645, 1617, 1565, 1500, 1428

NMR (DMSO-d₆)δ: 0.79–1.06 (8H, m) 2.06–2.21 (2H, m), 2.22(3H, s), 4.82 (2H, d, J=18.2 Hz), 4.99 (1H, d, J=8.0Hz), 4.99 (1H, d, J=18.2 Hz), 6.68–6.79 (1H, m), 6.85 (1H, d, J-8.0Hz), 7.09 (1H, d, J=5.2 Hz), 7.18 (1H, s), 7.28–7.50 (5H, m), 9.03 (1H, s).

Elemental Analysis (For $C_{27}H_{28}N_4O_5 \cdot 0.1H_2O$)

Calcd.: C, 66.14; H, 5.80; N, 11.43

Found: C, 66.05; H, 5.80; N, 11.46.

EXAMPLE 6

1,5-Bis-(2-triphenylmethyltetrazol-5-ylmethyl)-3-(N'-(m-tolyl)ureido)-1H-1,5-benzodiazepine-2,4(3H,5H)-dione 8k Yield, 49.3%; m.p. =156°–158° C.

IR $v_{max}$(KBr): 3411, 1711, 1678, 1612, 1597, 1546 cm⁻¹.

NMR (CDCl₃) δ: 2.27 (3H, s), 4.89 (2H, d, J=16.4 Hz), 5.05 (2H, d, J=16.4 Hz), 5.28 (1H, d, J=7.8 Hz), 6.24 (1H, d, J=7.8 Hz), 6.70–7.50 (39H, m).

Elemental Analysis (for $C_{59}H_{48}N_{12}O \cdot 3H_2O$)

Found: C, 71.28; H, 5.15; N, 17.65

Calcd.: C, 71.50; H, 5.08; N, 16.96.

EXAMPLE 7

1,5-Bis-(tetrazol-5-ylmethyl)-3-(N'-(m-tolyl)-ureido)-1H-1,5-benzodiazepine-2,4-(3H,5H)-dione 8l To a solution of Compound 8k (353 mg, 0.363 mmol) in methanol (20 ml) is added 10% HCl (5 ml) and the mixture is stirred for 15 hr at room temperature. After the addition of water (150 ml), the mixture is extracted with ethyl acetate. The organic layer is washed with water and extracted with 10% aqueous sodium carbonate. The aqueous layer is acidified with 10% HCl and extracted with ethyl acetate. The extract is washed with water, dried over sodium sulfate, and distilled under reduced pressure to remove the solvent. Crystallization from methanol/benzene gives Compound 8l (118 mg, 66.7%).

M.p. =228–230° C.

IR $v_{max}$(KBr): 3375, 3274, 1713, 1688, 1647, 1561 cm⁻¹.

NMR (CDCl₃)δ: 2.29 (3H, s), 5.22 (1H, s), 5.37 (2H, d, J=16.4 Hz), 5.41 (2H, d, J=16.4 Hz), 6.83 (1H, m), 7.09–7.20 (3H, m), 7.45 (4H, m).

Elemental Analysis (for $C_{21}H_2ON_{12}O_3$)

Found: C, 51.51; H, 4.23; N, 34.36

Calcd.: C, 51.64; H, 4.13; N, 34.41.

EXAMPLE 8

Disodium 1,5-bis-(tetrazol-5-ylmethyl)-3-(N'-(m-tolyl)ureido)-1H-1,5-benzodiazepine-2,4(3H,5H)-dione 8m Disodium salt 8m is obtained quantitatively by lyophilizing a solution of Compound 8l (85.8 mg, 0.176 mmol) in aqueous 0.1N NaOH solution (3.50 ml).

IR $v_{max}$ (KBr): 3380, 1700, 1669, 1613, 1559 cm⁻¹.

NMR (DMSO-d₆)δ: 2.21 (3H, s), 4.83 (2H, d, J=15.6 Hz), 4.92 (1H d, J=8.2 Hz), 5.24(2H, d, J=15.6 Hz), 6.70 (1H d, J=5.0 Hz), 6.80 (1H, d, J=8.2 Hz), 7.01–7.13 (2H,m), 7.18 (1H, s), 7.29 (2H, m), 7.88 (2H, m), 9.07 (1H, s).

Elemental Analysis (for $C_{21}H_{18}N_{12}O_3Na_2 \cdot 1.6H_2O$)

Found: C, 44.80; H, 3.39; N, 30.09; Na, 8.26

Calcd.: C, 44.94; H, 3.81; N, 29.95; Na, 8.19.

Compounds 8n, 8o, 8p and 8q described in the following Examples were prepared from corresponding starting materials in a manner similar to that described in Example 1 above.

EXAMPLE 9

1b 1,5-Bis-allyl-3-{N'-(m-tolyl)ureido}-1H-1,5-benzodiazepine-2,4(3H,5H)-dione 8n M.p. =210°–211° C.

IR $v_{max}$ (nujol): 3327, 1702, 1666, 1641, 1561 cm⁻¹

NMR (DMSO-d₆)δ: 2.22 (3H, s), 4.45 (2H, dd, J=15.9 & 6.0 Hz), 4.67 (2H, dd, J=15.9 & 6.0 Hz), 4.90 (1H, d, J=7.6 Hz), 5.04–5.10 (2H, m), 5.14 (2H, d, J=3.0Hz), 5.59–5.82 (2H, m), 6.68–6.78 (1H, m), 6.88 (1H, d, J=7.6 Hz), 7.08–7.14 (2H, m), 7.17 (1H, s), 7.35–7.48 (2H, m), 7.55–7.68 (2H, m), 9.08 (1H, s).

Elemental Analysis (for $C_{23}H_{24}N_4O_3 \cdot 0.3H_2O$)

Found: C, 67.50; H, 6.02; N, 13.65

Calcd.: C, 67.40; H, 6.05; N, 13.67.

EXAMPLE 10

1,5-Bis-(cyclopropylmethyl)-3-{N'-(m-tolyl)-ureido}-1H-1,5-benzodiazepine-2,4(3H,5H)-dione 8o M.p. =221°–222° C.

IR $v_{max}$ (nujol): 3315, 1693, 1643, 1611 cm⁻¹.

NMR (DMSO-d₆)δ: 0.09–0.18 (4H, m), 0.23–0.37(4H, m), 0.72–0.92 (2H, m), 2.22 (3H, s), 3.66 (2H, dd, J=14.2, 6.8 Hz), 4.16 (2H, dd, J=14.2, 6.8 Hz), 4.79 (1H, d, J=7.6 Hz), 6.67–6.76 (1H, m), 6.84(1H, d, J=7.8 Hz), 7.10 (2H, dd, J=3.0, 1.0 Hz), 7.18 (1H, s), 7.37–7.51 (2H, m), 7.66–7.78 (2H, m), 9.09 (1H, s).

Elemental Analysis (for $C_{25}H_{28}N_4O_3 \cdot 0.4H_2O$)

Found: C, 68.40; H, 6.50; N, 12.81

Calcd.: C, 68.29; H, 6.60; N, 12.74.

EXAMPLE 11

1,5-Bis-(o-methylbenzyl)-3-{N'-(m-tolyl)-ureido}-1H-1,5-benzodiazepine-2,4(3H,5H)-dione 8p M.p. =225°–227° C.

IR $v_{max}$ (nujol): 3334, 1701, 1688, 1641 cm⁻¹.

NMR (DMSO-d₆)δ: 2.12 (6H, s), 2.25 (3H, s), 4.99 (2H, d, J=16.4 Hz), 5.09 (2H, d, J=16.4 Hz), 5.16 (1H, d, J=7.4 Hz), 6.75 (1H, d, J=6.2 Hz), 6.88–7.23 (12H, m), 7.28–7.37 (2H, m), 7.45–7.56 (2H, m), 9.11 (1H, s).

Elemental Analysis (for $C_{33}H_{32}N_4O_3$)

Found: C, 74.19; H, 6.15; N, 10.34

Calcd.: C, 74.41; H, 6.06; N, 10.52.

EXAMPLE 12

1,5-Bis-(m-BOC-aminophenylmethyl)-3-(N'-(m-tolyl)ureido)-1H-1,5-benzodiazepine-2,4(3H,5H)-dione 8q Yield, 65.3%.

IR $v_{max}$ (KBr): 3413, 1703, 1675, 1612, 1547 cm⁻¹.

NMR (CDCl$_3$)δ: 1.50 (18H, s), 2.10 (3H, s), 4.90 (4H, s), 5.47 (1H, d, J=8.2 Hz), 6.62 (2H, t, J=7.4 Hz), 6.70 (2H, d, J=8.0 Hz), 6.87 (1H, d J=7.8 Hz), 6.87 (1H, d, J=7.8 Hz), 6.92 (1H, s), 7.04 (11H, m), 7.61 (2H, d, J=8.2 Hz), 7.60 (1H, s).

Elemental Analysis (for C$_{41}$H$_{46}$N$_6$O$_7$·0.5H$_2$O)
Found: C, 66.31; H, 6.51; N, 11.08
Calcd.: C, 66.20; H, 5.37; N, 11.30.

EXAMPLE 13

1,5-Bis-(aminophenylmethyl)-3-(N'-(m-tolyl)ureido)-1H-1,5-benzodiazepine-2,4(3H,5H)-dione 8r To a solution of Compound 8q (360 mg, 0.490 mmol) in ethyl acetate (4 ml) is added a solution (2 ml) of 4N HCl in ethyl acetate and the mixture is stirred for 5 hr at room temperature. Crystals are filtered off to obtain the objective compound (295 mg, 99.0%).

M.p.=176°–179° C.

IR ν$_{max}$ (KBr): 3416, 2864, 2591, 1697, 1663, 1603, 1557 cm$^{-1}$.

NMR (CD$_3$OD)δ: 2.29 (3H, s), 5.06 (2H, d, J=16.2 Hz), 5.25 (1H, s), 5.25 (2H, d, J=16.2 Hz), 6.84 (1H, m), 7.11–7.18 (3H, m), 7.25–7.56 (12H, m).

Elemental Analysis (for C$_{31}$H$_{32}$N$_6$O$_3$C$_{12}$·H$_2$O)
Found: C, 59.43; H, 5.69; N, 13.16; Cl, 11.54
Calcd.: C, 59.52; H, 5.48; N, 13.43; Cl, 11.33.

Compounds 8s and 8t described in the following Examples were prepared from corresponding starting materials in a manner similar to that described in Example 1 above.

EXAMPLE 14

1,5-Bis-(t-butoxycarbonylmethyl)-3-(N'-(m-tolyl)ureido)-1H-1,5-benzodiazepine-2,4(3H,5H)-dione 8s Yield 37.3%; m.p.=218°–219° C.

IR ν$_{max}$ (KBr): 3370, 1742, 1708, 1653, 1615, 1570, 1500, 1422, 1370, 1225, 1155 cm$^{-1}$.

NMR (CDCl$_3$—CD$_3$OD)δ: 1.44 (18H, s)2.28, (3H, s), 4.46, (4H, q, J=9.8 Hz), 5.30 (1H, s), 6.16–6.30 (1H, br.s), 6.71–6.88 (2H, m), 7.03–7.23 (3H, m), 7.36(4H, m).

Elemental Analysis (for C$_{29}$H$_{36}$N$_4$O·2H$_2$O)
Found: C, 62.59; H, 6.60; N, 10.10
Calcd.: C, 62.62; H, 6.60; N, 10.07.

NMR (CDCl$_3$+CD$_3$OD)δ: 2.28 (3H, s), 3.59 (2H, m), 3.76 (4H, m), 4.61 (2H, m), 5.12 (1H, s), 6.80 (1H, m), 7.12 (2H, m), 7.21 (1H, s), 7.43 (4H, m).

EXAMPLE 15

1,5-Bis-(2-hydroxymethyl)-3-(N'-(m-tolyl)ureido)-1H-1,5-benzodiazepine-2,4(3H,5H)-dione 8t M.p.=221°–224° C.

IR ν$_{max}$ (KBr): 3437, 3387, 1701, 1629, 1561 cm$^{-1}$.

NMR (CDCl$_3$+CD$_3$OD)δ: 2.28 (3H, s), 3.59 (2H, m), 3.76 (4H, m), 4.61 (2H, m), 5.12 (1H, s), 6.80 (1H, m), 7.12 (2H, m), 7.21 (1H, s), 7.43 (4H, m).

Elemental Analysis (for C$_{21}$H$_{24}$N$_4$O$_3$·0.2H$_2$O)
Found: C, 60.53; H, 5.92; N, 13.55
Calcd.: C, 60.63; H, 5.91; N, 13.47.

EXAMPLE 16

1,5-Bis-(carboxymethyl)-3-(N'-(m-tolyl)ureido)-1H-1,5-benzodiazepine-2,4(3H,5H)-dione 8u To a solution of Compound 8t (193 mg, 0.468 mmol) in acetone (24 ml) is added dropwise Jones' reagent (3M, 1 ml) and mixture is stirred for 2 hr at 55° C. After cooling, water is added to the mixture. The mixture is extracted with chloroform/methanol (4:1) to obtain a crude carboxylic acid (166 mg, 80.6%).

NMR (CDCl$_3$+CD$_3$OD)δ: 2.27 (3H, s), 4.50 (2H, d, J=17.6 Hz), 4.55 (2H,d , J=17.6 Hz ), 5.30 (1H, s), 6.80 (1H, m), 7.11 (2H, m), 7.19 (1H, m), 7.41 (4H, m).

EXAMPLE 17

1,5-Bis-(pyrrolidinecarbonylmethyl)-3-(N'-(3-(3-(carbomethoxy) propylcarbamoyloxymethyl)phenyl)ureido)-1H-1,5-benzodiazepine-2,4(3H,5H) -dione 9a Compound 6 is prepared in a manner similar to that described in Preparation 4 for the preparation of Compound 5 using Compound 4 prepared in Preparation 3 and 3-(3-(carbomethoxy)propylcarbamoyloxymethyl)phenyl-isocyanate. Compound 9a is then prepared in a manner similar to that described in Preparation 10 for the preparation of Compound 14 h using Compound 6 and pyrrolidinocarbonylmethyl bromide.

IR ν$_{max}$ (CHCl$_3$)δ: 3433, 3372, 1708, 1656, 1599, 1558 cm$^{-1}$.

NMR (CDCl$_3$) δ: 1.73–2.02 (10H, m), 2.36 (2H, t, J=7.2 Hz), 3.19 (2H, m), 3.30–3.53 (8H, m), 3.66 (3H, s), 4.57 (2H, d, J=16.8 Hz), 4.62 (2H, d, J=16.8 Hz), 4.96 (2H, s), 5.21 (1H, d, J=6.2 Hz), 5.49 (1H, br. s), 6.49 (1H, d, J=7.6 Hz), 6.86 (1H, d, J=7.0 Hz), 7.12 (1H, d, J=7.8 Hz), 7.23–7.40 (4H, m), 7.50 (2H, m), 7.98 (1H, s).

Elemental Analysis (for C$_{35}$H$_{43}$N$_7$O$_9$·0.9H$_2$O)
Found: C, 58.29; H, 6.15; N, 13.58
Calcd. : C, 58.23; H, 6.25; N, 13.58.

Compounds 9b, 9d, 9f, 9g, 9h, 9i, 9n, 9o, 9t, 9u, 10c, 10j, 10k, 10s, 10t and 10u described in the following Examples were prepared in a manner similar to that described in Example 17 from corresponding starting materials.

EXAMPLE 18

1,5-Bis-(thiazolidinecarbonylmethyl)-3-(N'-(3-(3-(carbomethoxy)propylcarbamoyloxymethyl)phenyl)ureido)-1H-1,5-benzodiazepine-2,4(3H,5H)-dione 9b IR ν$_{max}$ (CHCl$_3$): 3431, 3374, 1709, 1663, 1598, 1558 cm$^{-1}$.

NMR (CDCl$_3$)δ: 1.82 (2H, qui, J=7.0 Hz), 2.35 (2H, t, J=7.3 Hz), 2.95 (2H, t, J=6.1 Hz), 3.07 (2H, m), 3.19 (2H, m), 3.66 (3H, s), 3.69 (2H, m), 3.82 (2H, t, J=6.2 Hz), 4.38–4.70 (8H, m), 4.97 (2H, s), 5.24 (1H, br.s), 5.42 (1H, br.s), 6.55 (1H, br.s), 6.89 (1H, d, J=7.8 Hz), 7.14 (1H, d, J=7.8 Hz), 7.23–7.52 (7H, m), 7.88 (1H, s).

Elemental Analysis (for C$_{33}$H$_{39}$N$_7$O$_9$S$_2$)
Found: C, 52.68; H, 5.43; N, 12.91; S, 7.83
Calcd.: C, 52.66; H, 5.38; N, 13.03; S, 8.52.

EXAMPLE 19

1,5-Bis-(o-methylphenacyl)-3-(N'-(3-(3-(carbomethoxy)propylcarbamoyloxymethyl)phenyl)ureido)-1H-1,5-benzodiazepine-2,4(3H,5H)-dione 9d M.p.=162°–164° C.

IR ν$_{max}$ (nujol): 3353, 1703, 1689, 1527 cm$^{-1}$.

NMR (DMSO-d₆)δ: 1.81 (2H, quintet, J=7.4 Hz), 2.34 (2H, t, J=7.4 Hz), 2.35 (6H, s), 3.18 (2H, q, J=6.6 Hz), 3.65 (3H, s), 4.91 (2H, s), 4.97 (4H, s), 5.25–5.36 (1H, br.s), 5.40 (1H, d, J=6.6 Hz), 6.66–6.77 (1H, br.s), 6.79–6.88 (1H, m), 7.00–7.65 (16H, m).

Elemental Analysis (for $C_{41}H_{41}N_5O_9$)

Found: C, 65.59; H, 5.58; N, 9.34

Calcd.: C, 65.85; H, 5.53; N, 9.37.

EXAMPLE 20

1,5-Bis-(2-furylcarbonylmethyl)-3-(N'-(3-(3-(carbomethoxy)propylcarbamoyloxymethyl)phenyl)ureido)-1H-1,5-benzodiazepine-2,4(3H,5H)-dione 9f M.p.=176°–178° C.

IR $v_{max}$ (nujol): 3346, 3122, 1727, 1706, 1685, 1570 cm⁻¹.

NMR (CDCl₃)δ: 1.81 (2H, quintet, J=7.0 Hz), 2.34 (2H, t, J=7.4 Hz), 3.18 (2H, q, J=6.0 Hz), 3.65 (3H, s), 4.98 (2H, s), 5.11 (2H, d, J=17.8 Hz), 5.28 (2H, d, J=17.8 Hz), 5.44 (1H, d, J=7.0 Hz), 6.56 (2H, d.d, J=1.8 & 0.6 Hz), 6.90 (1H, d, J=7.2 Hz), 7.09–7.43 (11H, m), 7.61 (2H, d.d, J=0.6 & 0.6 Hz).

Elemental Analysis (for $C_{35}H_{33}N_{11}\cdot 0.5H_2O$)

Found: C, 59.33; H, 4.75; N, 9.75

Calcd.: C, 59.32; H, 4.84; N, 9.88.

EXAMPLE 21

1,5-Bis-(2-thienylcarbonylmethyl)-3-(N'-(3-(3-(carbomethoxy)propylcarbamoylmethyl)phenyl)ureido)-1H-1,5-benzodiazepine-2,4(3H,5H)-dione 9g M.p.=197°–198° C.

IR $v_{max}$ (nujol): 3338, 1705, 1679, 1667, 1637, 1568 cm⁻¹.

NMR (DMSO-d₆)δ: 1.64 (2H, qui, J=7.0Hz), 2.30(2H, t, J=7.4 Hz), 3.00 (2H J=5.8 Hz), 3.57 (3H, s), 4.93 (2H, s), 5.12 (1H, d, J=7.8 Hz), 5.28 (2H, d, J=18.0 Hz), 5.56 (2H, J=18.0Hz), 6.84–6.96 (2H, m), 7.12–7.55 (1OH, m) 8.08–8.22 (4H, m), 9.18 (1H, s).

Elemental Analysis (for $C_{35}H_{33}N_5O_9S_2\cdot 0.5H_2O$)

Found: C, 56.60; H, 4.54; N, 9.34; S, 8.91

Calcd.: C, 56.75; H, 4.63; N, 9.45; S, 8.66.

EXAMPLE 22

1,5-Bis-(cyclopropylcarbonylmethyl)-3-(N'-(3-(3-(carbomethoxy)propylcarbamoyloxymethyl)phenyl)ureido)-1H-1,5-benzodiazepine-2,4(3H,5H)-dione 9h IR $v_{max}$(KBr): 3387, 3367, 1711, 1691, 1615, 1598, 1556, 1502 cm⁻¹.

NMR (DMSO-d₆)δ: 0.80–1.08 (8H, m), 1.64 (2H, qui, J=7.1 Hz), 2.15 (2H, m), 2.30 (2H, t, J=7.4 Hz), 2.99 (2H, q, J=6.2 Hz), 3.57 (3H, s), 4.84 (2H, d, J=18.0 Hz),4.92 (2H, s), 4.99 (2H, d, J=18.0 Hz), 4.99 (1H, d, J=8.0Hz), 6.88 (2H, m), 7.15–7.47 (8H, m), 9.16 (1H, s).

Elemental Analysis (for $C_{33}H_{37}N_5O_9\cdot H_2O$)

Found: C, 59.62; H, 5.74; N, 10.22

Calcd.: C, 59.54; H, 5.90; N, 10.52.

EXAMPLE 23

1,5-Bis-(cyclopentylcarbonylmethyl)-3-(N'-(3-(3-(carbomethoxy)propylcarbamoyloxymethyl)phenyl)ureido)-1H-1,5-benzodiazepine-2,4(3H,5H)-dione 9i IR $v_{max}$(KBr): 3382, 1723, 1702, 1614, 1598, 1557 cm⁻¹.

NMR (CDCl₃)δ: 1.45–2.00 (18H, m), 2.36 (2H, t, J=7.2 Hz), 2.94 (2H, qui, J=7.9 Hz), 3.20 (2H, q, J=6.5 Hz), 3.67 (3H, s), 4.68 (2H, d, J=18.0Hz), 4.79 (2H, d, J=18.0Hz), 4.97 (2H, s), 5.24 (1H, br.s), 5.30 (1H, d, J=7.4 Hz), 6.45 (1H, d, J=7.4 Hz), 6.90 (1H, d, J=7.4 Hz), 7.09–7.35 (7H, m), 7.39 (1H, s).

Elemental Analysis (for $C_{37}H_{45}N_5O_9\cdot 0.5H_2O$)

Found: C, 62.26; H, 6.43; N, 10.04

Calcd.: C, 62.35; H, 6.50; N, 9.83.

EXAMPLE 24

1,5-Bis-allyl-3-(N'-(3-(3-(carbomethoxy)-propylcarbamoyloxymethyl)phenyl)ureido)-1H-1,5-benzodiazepine-2,4(3H,5H)-dione 9n M.p.=196°–197° C.

IR $v_{max}$ (nujol): 3423, 3288, 1729, 1689, 1638 cm⁻¹.

NMR (DMSO-d₆)δ: 1.83 (2H, quintet, J=6.8 Hz), 2.36 (2H, t, J=7.4 Hz), 3.21 (2H, q, J=7.0Hz), 3.67 (3H, s), 4.54 (4H, brs), 4.95 (2H, s), 5.16 (2H, s), 5.23 (1H, d, J=6.0 Hz), 5.25 (2H, s), 5.73–5.96 (2H, m), 6.64–6.76 (1H, m), 6.90 (1H, d, J=6.6 Hz), 7.05–7.36 (6H, m), 7.40–7.58 (3H, m).

Elemental Analysis (for $C_{29}H_{33}N_5O_7$)

Found: C, 61.57; H, 5.89; N, 12.43

Calcd.: C, 61.80; H, 5.90; N, 12.43.

EXAMPLE 25

1,5-Bis-(cyclopropylmethyl)-3-(N'-(3-(3-(carbomethoxy)propylcarbamoyloxymethyl)phenyl)ureido)-1H-1,5-benzodiazepine-2,4(3H,5H)-dione 9o M.p.=215°–216° C.

IR $v_{max}$ (nujol): 3421, 2184, 1729, 1685, 1637 cm⁻¹.

NMR (DMSO-d₆) 0.09–0.18 (4H,m), 1.64 (2, quintet, J=7.0Hz), 2.30 (2H, t, J=7.4 Hz), 2.99 (2H, q, J=6.6 Hz), 3.57 (3H, s), 3.66 (2H, d.d, J=14.0 & 7.0 Hz), 4.16 (2H, d.d, J=14.0 & 7.0Hz), 4.79 (1H, d, J=7.4 Hz), 4.91 (2H, s), 6.77–6.91 (2H, m), 7.13–7.32 (3H, m), 7.35, (1H, s), 7.38–7.49 (2H, m), 7.67–7.78 (2H, m), 9.21 (1H, s).

Elemental Analysis (for $C_{31}H_{37}N_5O_7\cdot 0.3H_2O$)

Found: C, 62.64; H, 6.28; N, 11.76

Calcd.: C, 62.36; H, 6.35; N, 11.73.

EXAMPLE 26

1,5-Bis-(2-hydroxyethyl)-3-(N'-(3-(3-(carbomethoxy)propylcarbamoyloxymethyl)phenyl)ureido)-1H-1,5-benzodiazepine-2,4(3H,5H)-dione 9t M.p.=147°–149° C.

IR v_{max} (KBr): 3412, 3308, 1725, 1691, 1664, 1642, 1599, 1565 cm$^{-1}$.

NMR (CDCl$_3$+CD$_3$OD)δ: 1.81 (2H, qui, J=7.1 Hz), 2.36 (2H, t, J=7.4 Hz), 3.18 (2H, t, J=6.9 Hz), 3.48–3.83 (6H, m), 3.66 (3H, s), 4.63 (2H, m), 4.97 (2H, s), 5.11 (1H, s), 6.91 (1H, d, J=7.2 Hz), 7.12–7.53 (7H, m).

Elemental Analysis (for C$_{27}$H$_{33}$N$_5$O$_9$·0.3H$_2$O)
Found: C, 56.15; H, 5.92; N, 12.32
Calcd.: C, 56.21; H, 5.87; N, 12.14.

EXAMPLE 27

1,5-Bis-(carboxymethyl)-3-(N'-(3-(3-(carbomethoxy)propylcarbamoyloxymethyl)phenyl)ureido)-1H-1,5-benzodiazepine-2,4(3H,5H)-dione 9u NMR (CDCl$_3$+CD$_3$OD)δ: 1.81 (2H, qui, J=7.0 Hz), 2.36 (2H, t, J=7.4 Hz), 3.18 (2H, t, J=7.1 Hz), 3.66 (3H, s), 4.49 (2H, d, J=17.6 Hz), 4.56 (2H,d, J=17.6 Hz), 5.00 (2H, s), 5.30 (1H, s), 6.93 (1H, d, J=7.4 Hz), 7.13–7.52 (7H, m).

EXAMPLE 28

1,5-Bis-(cyclopropylcarbamoylmethyl)-3-(N'-(3-(3-(benzoyloxycarbonyl)propylcarbamoyloxymethyl)-phenyl)ureido)-1H-1,5-benzodiazepine-2,4 (3H,5H)-dione 10c IR v_{max} (CHCl$_3$): 3333, 1710, 1668, 1614, 1599, 1560, 1521 cm$^{-1}$.

NMR (CDCl$_3$+CD$_3$OD)δ: 0.44 (4H, m), 0.67 (4H, m), 1.84 (2H, qui, J=7.1 Hz), 2.41 (2H, t, J=7.5 Hz), 2.63 (2H, m), 3.19 (2H, t, J=6.8 Hz), 4.34(2H, d, J=16.2 Hz), 4.70 (2H, d, J=16.2 Hz), 5.00 (2H, s), 5.11 (2H, s), 5.13 (1H, s), 6.93 (1H, d, J=7.2 Hz), 7.14–7.52 (12H, m).

Elemental Analysis (for C$_{39}$H$_{43}$N$_7$O$_9$·0.6H$_2$O)
Found: C, 61.28; H, 5.75; N, 12.83
Calcd.: C, 61.62; H, 5.83; N, 12.82.

EXAMPLE 29

1,5-Bis-(1-methylimidazol-2-ylmethyl)-3-(N'-(3-(3-(benzoyloxycarbonyl)propylcarbamoyloxymethyl)-phenyl)ureido)-1H-1,5-benzodiazepine-2,4(3H,5H)-dione 10j Compound 10j is prepared using 1-methyl-2-chloromethylimidazole (T. S. Manoharan and R. S. Brown, J. Org. Chem., 54, 1439 (1989)) as a starting material in 84.9 % yield.

NMR (CDCl$_3$)δ: 1.81 (2H, qui, J=7.0Hz), 2.38 (2H, t, J=7.5 Hz), 3.16 (2H, t, J=6.6 Hz), 3.53 (6H, s), 4.91–5.19 (5H, m), 4.94 (2H, s), 5.10 (2H, s), 5.44 (1H, t, J=4.6 Hz), 6.74 (3H, s), 6.86 (2H, s), 6.89 (1H, s), 7.11 (1H, t, J=7.6 Hz), 7.18–7.37 (5H, m), 7.33 (5H, s), 7.76 (2H, m), 8.10 (1H, br.s).

Elemental Analysis (for C$_{39}$H$_{41}$N$_9$O$_7$·0.6H$_2$O)
Found: C, 61.77; H, 5.69; N, 16.76
Calcd.: C, 61.75; H, 5.61; N, 16.62.

EXAMPLE 30

1,5-Bis-(2-triphenylmethyltetrazol-5-yl)-3-(N'-(3-(3-(benzyloxycarbonyl)propylcarbamoyloxymethyl)-phenyl)ureido)-1H-1,5-benzodiazepine-2,4(3H,5H)-dione 10k Yield, 75.5%.

IR v_{max}(KBr): 3405, 1714, 1639, 1614, 1599, 1558 cm$^{-1}$.

NMR (CDCl$_3$)δ: 1.81 (2H, qui, J=7.2 Hz), 2.37 (2H, t, J=7.3 Hz), 3.16 (2H, q, J=6.6 Hz), 4.88 (2H, d, J=16.4 Hz), 4.96 (2H, s), 5.06 (2H, d, J=16.4 Hz), 5.09 (2H, s), 5.16 (1H, m), 5.28 (1H, d, J=7.6 Hz), 6.45 (1H, d, J=7.6 Hz), 6.89–7.02 (12H, m), 7.08–7.38 (30H, m), 7.45 (2H, m).

Elemental Analysis (for C$_{71}$H$_{61}$N$_{13}$O$_7$·0.7H$_2$O)
Found: C, 69.88; H, 5.34; N, 14.96
Calcd.: C, 69.85; H, 5.15; N, 14.91.

EXAMPLE 31

1,5-Bis-(tert-butoxycarbonylmethyl)-3-(N'-(3-(3-(benzyloxycarbonyl)propylcarbamoyloxymethyl)phenyl)-ureido)-1H-1,5-benzodiazepine-2,4(3H,5H)-dione 10s Yield, 94.3%.

IR v_{max} (KBr): 3385, 1739, 1711, 16147, 1598, 1558 cm$^{-1}$.

NMR (CDCl$_3$) δ: 1.44 (18H, s), 1.84 (2H, qui, J=7.1 Hz), 2.41 (2H, t, J=7.5 Hz), 3.20 (2H, q, J=6.0 Hz), 4.37 (2H, d, J=17.2 Hz), 4.56 (2H, d, J=17.2 Hz), 4.93 (2H, s), 5.11 (2H, s), 5.28 (1H, br.s), 5.33 (1H, d, J=7.4 Hz), 6.60 (1H, d, J=8.2 Hz), 6.86 (1H, d, J=7.4 Hz), 7.05–7.40 (12H, m), 7.43 (1H, s).

Elemental Analysis (for C$_{41}$H$_{49}$N$_5$O$_{11}$·0.4H$_2$O)
Found: C, 61.97; H, 6.33; N, 8.86
Calcd.: C, 61.94; H, 6.31; N, 8.81.

EXAMPLE 32

1,5-Bis-(2-hydroxyethyl)-3-(N'-(3-(3-(benzyloxycarbonyl)propylcarbamoyloxymethyl)phenyl)-ureido)-1H-1,5-benzodiazepine-2,4(3H,5H)-dione 10t M.p.=138°–142° C.

IR v_{max} (CHCl$_3$): 3449, 3375, 1703, 1675, 1658, 1599, 1556 cm$^{-1}$.

NMR (CDCl$_3$+CD$_3$OD)δ: 1.83 (2H, qui, J=7.2 Hz), 2.41 (2H, t, J=7.4 Hz), 3.18 (2H, t, J=6.9 Hz), 3.51–3.66 (2H, m), 3.67–3.84 (4H, m), 4.52–4.70 (2H, m), 4.97 (2H, s), 5.11 (3H, s), 6.91 (1H, d, J=7.2 Hz), 7.17(1H, t, J=7.4 Hz), 7.22–7.42 (10H, m), 7.47 (2H, m).

Elemental Analysis (for C$_{33}$H$_{37}$N$_5$O$_9$·0.5H$_2$O)
Found: C, 60.35; H, 5.97; N, 10.83
Calcd.: C, 60.36; H, 5.83; N, 10.66.

EXAMPLE 33

1,5-Bis-(carboxymethyl)-3-(N'-(3-(3-(benzyloxycarbonyl)propylcarbamoyloxymethyl)-phenyl)ureido)-1H-1,5-benzodiazepine-2,4(3H,5H)-dione 10u NMR (CDCl$_3$+CD$_3$OD)δ: 1.84 (2H, qui, J=7.1 Hz), 2.41 (2H, t, J=7.2 Hz), 3.1–3.3 (2H, m), 4.49 (2H, d, J=18.0Hz), 4.56 (2H, d, J=18.0Hz), 5.01 (2H, s), 5.11 (1H, s), 5.30 (1H, s), 6.93 (1H, d, J=7.2 Hz), 7.14–7.50 (12H, m).

EXAMPLE 34

1,5-Bis-(pyrrolidinecarbonylmethyl)-3-(N'-(3-(3-(carboxy)propylcarbamoyloxymethyl)phenyl)ureido)-1H-1,5-benzodiazepine-2,4(3H,5H)-dione 11a To a solution of Compound 9a (243 mg, 0.344 mmol) in methanol (3.5 ml) is added a solution of lithium hydroxide monohydrate (35 mg, 0.834 mmol) in water (0.6 ml) and the mixture is stirred at room temperature for 7 hr. After the addition of water, the mixture is washed with chloroform. After acidifying with 10% HCl, the mixture is extracted with chloroform containing 10% methanol. The extract is washed with water, dried over sodium sulfate, and distilled under reduced pressure to remove the solvent to obtain Compound 11a (224 mg, 94.1%).

NMR (CDCl$_3$+CD$_3$OD$\delta$): 1.73–2.02 (10H, m), 2.34 (2H, t, J=7.3 Hz), 3.21 (2H, t, J=6.6 Hz), 3.40–3.56 (8H, m), 4.62 (4H, s), 5.03 (2H, s), 5.26 (1H, s), 6.90 (1H, d, J=7.0 Hz), 7.14–7.55 (7H, m).

Compounds 11 described in the following Examples were prepared in a manner similar to that described in Example 34 above.

EXAMPLE 35

1,5-Bis-(cyclopropylcarbamoylmethyl)-3-(N'-(3-(3-(carboxy)propylcarbamoyloxymethyl)phenyl)ureido)-1H-1,5-benzodiazepine-2,4(3H, 5H)-dione 11c NMR (CDCl$_3$+CD$_3$OD)$\delta$: 0.44 (4H, m), 0.67 (4H, m), 1.81 (2H, m), 2.34 (2H, t, J=7.2 Hz), 2.63 (2H, m), 3.1–3.3 (2H, m), 4.34 (2H, d, J=16.0 Hz), 4.70 (2H, d, J=16.0 Hz), 5.01 (2H, s), 5.13 (1H, s), 6.92 (1H, d, J=7.4 Hz), 7.14–7.46 (7H, m).

EXAMPLE 36

1,5-Bis-(o-methylphenacyl)-3-(N'-(3-(3-(carboxy)propylcarbamoyloxymethyl)phenyl)ureido)-1H-1,5-benzodiazepine-2,4(3H,5H)-dione 11d M.p.=174°–176° C.

IR $v_{max}$ (nujol): 3351, 3312, 1702, 1689, 1668, 1645, 1618, 1572 cm$^{-1}$.

NMR (DMSO-d$_6$)$\delta$: 1.61 (2H, quintet, J=7.0 Hz), 2.20 (2H, t, J=7.4 Hz), 2.36 (6H, s), 2.99 (2H, q, J=6.8 Hz), 4.93 (2H, s), 5.07(1H, d, J=8.0 Hz), 5.09 (2H, d, J=17.6 Hz), 5.20 (2H, d, J=17.6 Hz), 6.84–6.96 (2H, m), 7.16–7.41 (7H, m), 7.44–7.56 (6H, m), 7.75–7.83 (2H, m), 9.16 (1H,s).

Elemental Analysis (for C$_{40}$H$_{39}$N$_5$O$_9$·0.3H$_2$O)
Found : C,64.33; H, 5.28; N, 9.31
Calcd.: C,61.80; H, 6.15; N, 12.01.

EXAMPLE 37

1,5-Bis-(2-furylcarbonylmethyl)-3-(N'-(3-(3-(carboxy)propylcarbamoyloxymethyl)phenyl)ureido)-1H-1,5-benzodiazepine-2,4(3H,5H)-dione 11f M.p.=157°–160° C.

IR $v_{max}$ (nujol): 3507, 3439, 3345, 3127, 1707, 1679, 1664, 1651, 1618, 1571 cm$^{-1}$.

NMR (DMSO-d$_6$)$\delta$: 1.61 (2H, quintet, J=7.0 Hz), 2.21 (2H, t, J=7.2 Hz), 2.99 (2H, q, J=8.0Hz), 3.34 (2H, s), 4.92 (2H, s), 5.10 (1H, d, J=8.0Hz), 5.12 (2H, d, J=18.2 Hz), 5.38 (2H, d, J=18.2 Hz), 6.80 (2H, d.d, J=3.6 & 1.8 Hz), 6.87 (1H, s), 6.90 (1H, s), 7.13–7.54 (8H, m), 7.65 (2H, d.d, J=3.6 & 0.6 Hz), 8.10 (2H, d.d, J=1.8 & 0.6 Hz), 9.18 (1H, s).

Elemental Analysis (for C$_{34}$H$_{31}$N$_5$O$_{11}$·H$_2$O)
Found: C, 58.16; H, 4.68; N, 9.86
Calcd.: C, 58.04; H, 4.73; N, 9.95.

EXAMPLE 38

1,5-Bis-(2-thienylcarbonylmethyl)-3-(N'-(3-(3-(carboxy)propylcarbamoyloxymethyl)phenyl)ureido)-1H-1,5-benzodiazepine-2,4(3H,5H)-dione 11g M.p.=204°–207° C.

IR $v_{max}$ (KBr): 3340, 1705, 1666, 1637, 1614, 1568 cm$^{-1}$.

NMR (DMSO-d$_6$)$\delta$: 1.61 (2H, quintet, J=7.0Hz), 2.21 (2H, t, J=7.4 Hz), 2.99 (2H, q, J=5.8 Hz), 4.92 (2H, s), 5.12 (1H, s, J=8.0Hz), 5.29 (2H, d, J=18.0Hz), 5.56 (2H, d, J=18.0Hz), 6.81–6.97 (2H, m), 7.12–7.55 (1OH, m), 8.09–8.21 (4H, m), 9.19 (1H, s).

Elemental Analysis (for C$_{34}$H$_{31}$N$_5$O$_9$S$_2$·0.5H$_2$O)
Found : C, 56.40; H, 4.35; N, 9.49; S, 9.11
Calcd.: C, 56.19; H, 4.44; N, 9.64; S, 8.82.

EXAMPLE 39

1,5-Bis-allyl-3-(N'-(3-(3-(carboxy)propylcarbamoyloxymethyl)phenyl)ureido)-1H-1,5-benzodiazepine-2,4(3H,5H)-dione 11n M.p.=108°–112° C.

IR $v_{max}$ (nujol): 3311, 1695, 1664, 1640, 1616, 1598, 1563 cm$^{-1}$.

NMR (DMSO-d$_6$)$\delta$: 1.61 (2H, quintet, J=7.4 Hz), 2.20 (2H, t, J=7.4 Hz), 2.99 (2H, q, J=6.4 Hz), 4.45 (2H, d.d, J=16.0 & 5.8 Hz), 4.67 (2H, d.d, J=16.0 & 5.80Hz), 4.90 (1H, d, J=7.6 Hz), 4.92 (2H, s), 5.08 (2H, s), 5.15 (2H, d, J=3.2 Hz), 5.59–5.82 (2H, m), 6.83–6.95 (2H, m), 7.14–7.32 (3H, m), 7.34 (1H, s), 7.35–7.48 (2H, m), 7.55–7.68 (2H, m), 9.22 (1H, s).

Elemental Analysis (for C$_{28}$H$_{31}$N$_5$O$_7$·1.5H$_2$O)
Found : C, 60.02; H. 5.73; N, 12.60
Calcd.: C, 60.21; H. 5.77; N. 12.54.

EXAMPLE 40

1,5-Bis-(cyclopropylmethyl)-3-(N'-(3-(3-(carboxy)propylcarbamoyloxymethyl)phenyl)ureido)-1H-1,5-benzodiazepine-2,4(3H,5H)-dione 11o M.p.=147°–149° C.

NMR (DMSO-d$_6$)$\delta$: 0.04–0.17 (4H, m), 0.28–0.35 (4H, m), 0.72–0.92 (2H, m), 1.61 (2H, quintet, J=7.0Hz), 2.30 (2H, t, J=7.4 Hz), 2.99 (2H, q, J=6.6 Hz), 3.66 (2H, d.d, J=14.0 & 7.0Hz), 4.16 (2H, d.d, J=14.0 & 7.0 Hz), 4.79 (1H, d, J=7.4 Hz), 4.91 (2H, s), 6.77–6.91 (2H, m), 7.13–7.32 (3H, m), 7.35 (1H, s), 7.38–7.49 (2H, m), 7.67–7.78 (2H, m), 5 9.21 (1H, s).

Elemental Analysis (for C$_{30}$H$_{35}$N$_5$O$_7$S$_2$·0.3H$_2$O)
Found : C, 61.81; H. 6.11; N, 11.97
Calcd.: C, 61.80; H, 6.15; N, 12.01.

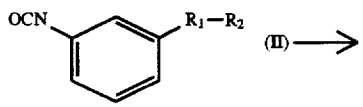

-continued

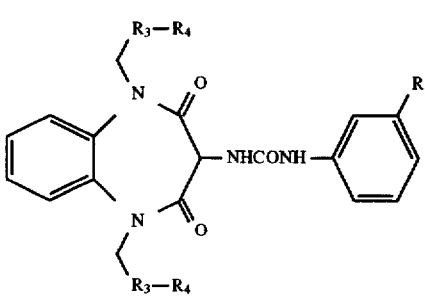

17-i ~ xvi: R₃—R₄ = —CO—△ (h)

18-i, iv, xii, xiii: R₃—R₄ = —CON⟩ (a)

19-iv: R₃—R₄ = —△ (o)

20-iv: R₃—R₄ = —CO—$\underset{S}{\text{⟩}}$ (g)

$R_1 - R_2$ = i: m-COOEt, ii: m-COOH, iii: m-CONHSO₂ipr,

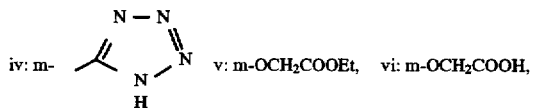

iv: m-  v: m-OCH₂COOEt, vi: m-OCH₂COOH,

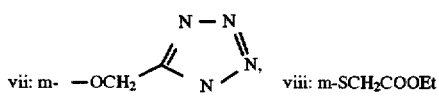

vii: m- —OCH₂—  viii: m-SCH₂COOEt

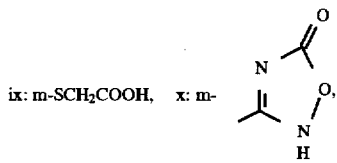

ix: m-SCH₂COOH, x: m- xi: m-SO₂NHCOCH₃, xii: m-CH₂COOMe, xiii: m-CH₂COOH, xiv: p-COOMe, xv: p-COOH, xvi: p-CN,

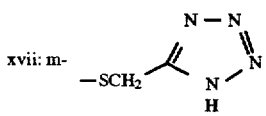

xvii: m- —SCH₂—

EXAMPLE 41

1,5-Bis-(cyclopropylcarbonylmethyl)-3-(N'-(m-carboethoxyphenyl))ureido)-1H-1,5-benzodiazepine-2,4(3H,5H)-dione 17-i To a solution of methyl 3-aminobenzoate (200 mg, 1.21 mmol) in tetrahydrofuran (10 ml) are added successively triphosgene (126 mg, 0.424 mmol) and triethylamine (354μ, 2.54 mmol). After stirring for 15 10 min, previously prepared amine 16 h (300 mg, 0.844 mmol) is added and the stirring is continued for another 3 hr. The reaction mixture is partitioned between a mixture of methylene chloride/methanol (5:1) and water. The organic layer is washed with water, dried over magnesium sulfate and concentrated under reduced pressure. The resultant crude product is purified by column chromatography on silica gel (toluene/ethyl acetate, 1:1) and recrystallized from a mixture of methylene chloride, methanol and diisopropyl ether to give the titled Compound 17i (320 mg; yield, 69%).

M.p.=222°–223° C.

IR $v_{max}$ (KBr): 3400, 1708, 1599, 1562, 1503, 1425 cm⁻¹.

NMR (DMSO-d₆)δ: 0.79–1.04 (8H, m), 1.29 (3H, t, J=7.0 Hz), 2.06–2.22 (2H, m), 4.28 (2H, q, J=7.0Hz), 4.83 (2H, d, J=18.0Hz), 5.00 (1H, d, J=7.8 Hz), 5.00 (2H, d, J=18.0 Hz), 6.89 (1H, d, J=7.8 Hz), 7.27–7.60 (7H, m), 8.60 (1H, s), 9.39 (1H, s).

Elemental Analysis (for C₂₉H₃₀N₄O₇·0.3H₂O)

Calcd.: C, 63.10; H, 5.59; N, 10.15

Found: C, 63.05; H, 5.61; N, 10.28.

EXAMPLE 42

1,5-Bis-(cyclopropylcarbonylmethyl)-3-(N'-(m-carboxyphenyl))ureido)-1H-1,5-benzodiazepine-2,4(3H,5H)-dione 17-ii Compound 17-ii is prepared by hydrolyzing the ester 17i obtained in Example 41 with an alkali in a conventional manner.

M.p.=274°–276° C.

IR $v_{max}$ (KBr): 3405, 1702, 1561, 1500, 1431 cm⁻¹.

NMR (DMSO-d6)δ: 0.75–1.05 (8H, m), 2.06–2.24 (2H, m), 4.83 (2H, d, J=18.2 Hz), 5.00 (1H, d, J=7.8 Hz), 5.00 (2H, d, J=18.2 Hz), 6.88 (1H, d, J=7.8 Hz), 7.27–7.55 (7H, m), 8.00 (1H, s), 9.30 (1H, s).

Elemental Analysis (for C₂₇H₂₆N₄O₇·0.5H₂O)

Calcd.: C, 61.47; H, 5.16; N, 10.62

Found: C, 61.47; H, 5.15; N, 10.62.

EXAMPLE 43

1,5-Bis-(cyclopropylcarbonylmethyl)-3-(N'-(m-(isopropylsulfonylaminocarbonyl)phenyl)ureido)-1H-1,5-benzodiazepine-2,4(3H,5H)-dione 17-iii Compound 17-iii is prepared in a manner similar to that described above using amine 16 h and 3-isopropylsulfonylaniline (disclosed in EP 0 508 796 A1) as starting materials.

M.p.=193°–194° C.

IR $v_{max}$ (KBr): 3380, 1700, 1602, 1553, 1503, 1432 cm⁻¹.

NMR (DMSO-d₆)δ: 0.80–1.05 (8H, m), 1.22 (6H, d, J=6.8 Hz), 2.06–2.23 (2H, m), 3.55–3.76 (1H, broad), 4.83 (2H, d, J=18.2 Hz), 5.00 (1H, d, J=8.0Hz), 5.00 (2H, d, J=18.2 Hz), 6.87 (1H, d, J=8.0 Hz), 7.21–7.56 (7H, m), 7.85 (1H, s), 9.33 (1H, s).

Elemental Analysis (for C₃₀H₃₃N₅O₈S·2.2H₂O)

Calcd.: C, 54.32; H, 5.68; N, 10.56; S, 4.83

Found: C, 54.16; H, 5.58; N, 10.69; S, 4.88.

EXAMPLE 44

1,5-Bis-(cyclopropylcarbonylmethyl)-3-(N'-(m-(tetrazoyl)phenyl)ureido)-1H-1,5-benzodiazepine-2,4(3H,5H)-dione 17-iv To a suspension of 3-amino-(1H-tetrazol-5-yl)benzene (disclosed in EP 0 508 796 A1) (195 mg, 1.21 mmol.) in tetrahydrofuran (10 ml) is added triethylamine (177 μl, 1.27 mmol) under ice-cooling and the mixture is stirred for 5 min. After addition of triphosgene (126 mg, 0.42 mmol) and triethylamine (354 μl, 2.54 mmol) in series, the reaction mixture is stirred for 15 min. To the mixture is added previously prepared amine 16 h (300 mg, 0.844 mmol) and the mixture is stirred at 0° C.for 30 min, then at room temperature for 3 hr. The reaction mixture is concentrated and partitioned between a mixture of methylene chloride-methanol (5:1) and water. The organic layer is dried over magnesium sulfate and concentrated under reduced pressure. The resultant crude product is purified by chromatography on silica gel (methylene chloride/methanol (5:1)) and recrystallized from a mixture of methanol and ether to give the titled Compound 17-iv (220 mg; yield, 48%) as white crystals.

M.p.=213°–215° C.

IR $v_{max}$(KBr): 3400, 1685, 1660, 1600, 1550, 1502, 1433 $cm^{-1}$.

NMR (DMSO-$d_6$)δ: 0.72–1.04 (8H, m), 2.06–2.25 (2H, m), 4.84 (2H, d, J=18.4 Hz), 5.01 (2H, d, J=18.4 Hz), 5.03 (1H, d, J=7.8 Hz), 6.93 (1H, d, J=7.8 Hz), 7.26–7.60 (8H, m), 8.04 (1H, s), 9.31 (1H, s).

Elemental Analysis (for $C_{27}H_{26}N_8O_5 \cdot 1.5H_2O$)

Calcd.: C, 56.94; H, 5.13; N, 19.67

Found: C, 56.72; H, 5.04; N, 19.38.

EXAMPLE 45

1,5-Bis-(cyclopropylcarbonylmethyl)-3-(N'-(m-(carboethoxymethoxy)phenyl)ureido)-1H-1,5-benzodiazepine-2,4(3H,5H)-dione 17-v 1) Ethyl 3-(N-tert-butyloxycarbonylamino)phenyloxyacetate To a solution of 3-aminophenol (2.18 g, 20 mmol) in tetrahydrofuran (10 ml) is added di-tert-butyl dicarbonate (4.578 g, 21 mmol) and the mixture is stirred for 15 hr at room temperature. To the residue obtained by concentrating the reaction mixture is purified by chromatography on silica gel (hexane/ethyl acetate (5:1)). To a solution of the resultant oily residue of 3-(N-tert-butyloxycarbonylamino)phenol in dimethylformamide are added ethyl 2-bromoacetate (2.44 ml, 22 mmol), potassium iodide (183 mg, 1.1 mmol) and potassium carbonate (3.04 g, 22 mmol) and the mixture is stirred for 15 hr at room temperature. The reaction mixture is concentrated under reduced pressure and the concentrate is partitioned between a mixture of ethyl acetate and water. The organic layer is dried over magnesium sulfate and concentrated under reduced pressure. The resultant crude product is purified by chromatography on silica gel (toluene/ethyl acetate (9:1)) to give the titled compound as colorless oil.

NMR (CDCl$_3$)δ: 1.22 (3H, t, J=7.4 Hz), 1.47 (9H, s), 4.17 (2H, q, J=7.4 Hz), 4.70 (2H, s), 6.47–6.57 (1H, m), 6.99–7.21(3H, m), 9.34 (1H, s).

2) Ethyl 3-aminophenyloxyacetate

To a solution of the compound prepared in 1) above in ethyl acetate (38 ml) is added 4N HCl (solution in ethyl acetate) (25 ml) and the mixture is stirred for 3 hr at room temperature. The crystalline precipitates are filtered off. The resultant crystals are dissolved in methylene chloride and washed with saturated aqueous sodium hydrogencarbonate solution. The organic layer is dried over magnesium sulfate and concentrated under reduced pressure to obtain the titled compound (1.744 g; yield from 3-aminophenol, 45%) as colorless oil.

NMR(CDCl$_3$) δ: 1.30 (3H, t, J=7.4 Hz), 4.27 (2H, q, J=7.4 Hz), 4.57 (2H, s), 6.23–6.38 (3H, m), 7.00–7.11 (1H, m).

The titled Compound 17-v is prepared in a manner similar to that described in Example 41 for the preparation of Compound 17i using 3-aminophenoxyacetic acid prepared in (2) above and the previously prepared amine 16 h.

M.p.=205°–206° C.

IR $v_{max}$ (KBr): 3370, 1760, 1700, 1642, 1608, 1602, 1562, 1500, 1455, 1428 $cm^{-1}$.

NMR (DMSO-$d_6$)δ: 0.77–1.08 (8H, m), 1.19 (3H, t, J=7.0Hz), 2.06–2.23 (2H, m), 4.15 (2H, q, J=7.0 Hz), 4.86 (2H, s), 4.83 (2H, d, J=18.0 Hz), 4.99 (1H, d, J=8.0Hz), 5.00 (2H, d, J=18.0Hz), 6.46 (1H, d.d, J=8.2 & 2.4 Hz), 6.79–6.92 (2H, m), 6.84 1H, s), 7.12 (1H, t, J=8.2 z), 7.27–7.50 (4H, m), 9.16 (1H, s).

Elemental Analysis (for $C_{30}H_{32}N_4O_8 \cdot 0.3H_2O$)

Calcd.: C, 61.91; H, 5.65; N, 9.63

Found: C, 61.91; H, 5.66; N, 9.61.

EXAMPLE 46

1,5-Bis-(cyclopropylcarbonylmethyl)-3-(N'-(m-(carboxymethoxy)phenyl)ureido)-1H-1,5-benzodiazepine-2,4(3H,5H)-dione 17-vi Compound 17-vi is prepared by hydrolyzing the ester 17-v obtained in Example 45 with an alkali in a conventional manner.

M.p.=257°–259° C.

IR Vx (KBr): 3400, 1755, 1698, 1650, 1620, 1565, 1425 $cm^{-1}$.

NMR (DMSO- $d_6$)δ: 0.77–1.03 (8H, m), 2.06–2.22 (2H, m), 4.57 (2H, s) 4.86 (2H, s), 4.82 (2H, d, J=18.2 Hz), 4.99 (1H, d, J=8.2 Hz), 4.99 (2H, d, J=18.2 Hz), 6.45 (1H, dd, J=6.8 & 2.0 Hz), 6.77–6.90 (2H, m) 7.06 (1H, brs.), 7.11 (1H, t, J=8.0 Hz), 7.28–7.49 (4H, m), 9.15 (1H, s).

Elemental Analysis (for $C_{28}H_{28}N_4O_8 \cdot 0.7H_2O$)

Calcd.: C, 59.93; H, 5.28; N, 9.98

Found: C, 59.93; H, 5.12; N, 9.97.

EXAMPLE 47

1,5-Bis-(cyclopropylcarbonylmethyl)-3-(N'-(m-(tetrazoylmethoxy)phenyl)ureido)-1H-1,5-benzodiazepine-2,4(3H,5H)-dione 17-vii 1) 3-Nitorphenoxyacetonitlile To a solution of 3-nitrophenol (6.955 g, 50 mmol) in dimethylformamide are added 97% bromoacetonitrile (6.944 g, 55 mmol), potassium iodide (457 mg, 2.75 mmol) and potassium carbonate (7.60 g, 55 mmol) and the mixture is stirred for 15 hr at room temperature. The reaction mixture is concentrated under reduced pressure and the concentrate is partitioned between a mixture of ethyl acetate and water. The organic layer is dried over magnesium sulfate and concentrated under reduced pressure. The resultant crude product is purified by chromatography on silica gel (toluene/ethyl acetate (9:1)) to give the titled compound (7.128 g; yield, 80%) as white crystals.

2) 3-(Tetrazo-5-yl)methoxyaniline

3-Nitorphenoxyacetonitlile obtained in 1) above is treated with sodium azide to convert the nitrile group into tetrazole group, followed by catalytic reduction, in accordance with the method described in EP 0 508 796 A1, page 19.

NMR(CD₃OD)δ: 5.36 (2H, s), 6.39–6.48 (3H, m), 7.05 (1H, t, J=0.8 Hz).

The titled compound is prepared in a manner similar to that described in Example 41 for the preparation of Compound 17i using 3-(tetrazo-5-yl)methoxyaniline prepared above and amine 16 h prepared in Preparation 15.

M.p.=203°–204° C.

IR $v_{max}$(KBr): 3380, 1700, 1605, 1558, 1502, 1430 cm$^{-1}$.

NMR (DMSO-d₆)δ: 0.78–1.06 (8H, m), 2.06–2.23 (2H, m), 4.80 (2H, d, J=18.2 Hz), 4.99 (1H, d, J=8.0Hz), 5.00 (2H, d, J=18.2 Hz), 5.40 (2H, s) 6.58 (1H, m), 6.81–6.94 (2H, m), 7.10–7.22 (2H, m), 7.26–7.49 (4H, m), 9.18 (1H, s).

Elemental Analysis (for $C_{28}H_{28}N_8O_6 \cdot 0.5H_2O$)

Calcd.: C, 57.83; H, 5.03; N, 19.27

Found: C, 57.90; H, 4.98; N, 19.24.

EXAMPLE 48

1,5-Bis-(cyclopropylcarbonylmethyl)-3-(N'-(m-(carboethoxymethylthio)phenyl)ureido)-1H-1,5-benzodiazepine-2,4(3H,5H)-dione 17-viii To a solution of the amine above (95 mg) in tetrahydrofuran (5 ml) is added triphosgene (50 mg) at 0° C. After adding triethylamine (40 μl) in 5 portions over 15 min, the mixture is stirred for 5 min at room temperature. The mixture is cooled again to 0° C. and a solution of amine 16 h (145 mg) in tetrahydrofuran (5 ml) is added thereto. After stirring for 1 hr at room temperature, ethyl acetate is added to the mixture. The reaction mixture is washed with 5% HCl and water in series, dried over sodium sulfate and distilled to remove the solvent. Crystallization of the resultant residue from methylene chloride/ether gives the titled Compound 17-viii (200 mg, 82.6%).

M.p.=193°–196° C.

IR $v_{max}$(KBr): 3379, 1716, 1699, 1649, 1609, 1587, 1545 cm$^{-1}$.

NMR (CDCl₃)δ: 0.87–1.16 (8H, m), 1.20 (3H, t, J=7.2 Hz), 2.00 (2H, m), 3.62 (2H, s), 4.14 (2H, q, J=7.2 Hz), 4.77 (2H, d, J=18.0Hz), 4.93 (2H, d, J=18.0 Hz), 5.34 (1H, d, J=7.4 Hz), 6.50 (1H, d, J=7.8 Hz), 6.98 (1H, dt, J=2.2, 6.6 Hz), 7.05–7.18 (2H, m), 7.20–7.36 (5H, m), 7.39 (1H,m).

Elemental Analysis (for $C_{30}H_{32}N_4O_7S \cdot 0.2H_2O$)

Calcd.: C, 60.43; H, 5.48; N, 9.40; S, 5.38

Found: C, 60.50; H, 5.55; N, 9.53; S, 5.34.

EXAMPLE 49

1,5-Bis-(cyclopropylcarbonylmethyl)-3-(N'-(m-(carboxymethylthio)phenyl)ureido)-1H-1,5-benzodiazepine-2,4(3H,5H)-dione 17-ix Compound 17-ix is prepared by hydrolyzing Compound 17-viii in a conventional manner.

IR $v_{max}$(KBr): 3382, 1705, 1673, 1638, 1601, 1589, 1547 cm$^{-1}$.

NMR (CDCl₃+CD₃OD)δ: 0.87–1.20 (8H, m),2.02 (2H, m), 7.00 (1H, dt, J=1.8, 7.4 Hz), 7.14 (1H, t, J=7.6 Hz), 7.23–7.39 (4H, m), 7.42 (1H, t, J=2.0 Hz).

Elemental Analysis (for $C_{28}H_{28}N_4O_7S \cdot 0.5H_2O$)

Calcd.: C, 58.68; H, 5.10; N, 9.77 ; S, 5.59

Found: C, 58.49; H, 5.26; N, 10.06; S, 5.63.

EXAMPLE 50

1,5-Bis-(cyclopropylcarbonylmethyl)-3-(N'-(m-(5-keto-1,2,4-oxadiazol-3-yl)phenyl)ureido)-1H-1,5-benzodiazepine-2,4(3H,5H)-dione 17-x Compound 17-x is prepared using m-(5-keto-1,2,4-oxadiazolyl)phenylisocyanate (lit., EP 0508796 A1) and amine 16 h in 53.4% yield.

IR $v_{max}$ (KBr): 3426, 1789, 1758, 1700,1640 cm$^{-1}$.

NMR (CDCl₃+CD₃OD)δ: 0.90–1.13 (6H, m), 1.19–1.33 (2H, m), 2.03 (2H, m), 4.61 (2H, d, J=18.0Hz), 5.17 (2H, d, J=18.0Hz), 5.45 (1H, d, J=7.8 Hz), 6.57 (1H, s), 6.94 (1H, dd, J=2.8, 8.0 Hz), 6.99 (1H, d, J=8.0Hz), 7.20 (2H, m),7.33 (1H, m), 7.40 (2H, m), 7.50 (1H, d, J=8.0Hz), 8.28 (1H, s), 10.98 (1H, s).

Elemental Analysis (for $C_{28}H_{26}N_6O_7S \cdot 0.5H_2O$)

Calcd.: C, 59.26; H, 4.79; N, 14.81

Found: C, 59.25; H, 4.99; N, 14.92.

EXAMPLE 51

1,5-Bis-(cyclopropylcarbonylmethyl)-3-(N'-(m-(acetylsulfamoyl)phenyl)ureido)-1H-1,5-benzodiazepine-2,4(3H,5H)-dione 17-xi Compound 17-xi is prepared in a manner similar to that described above using m-(acetylsulfamoyl)phenylisocyanate (lit., EP 0508796 A1) and amine 16 h in 31.0% yield.

IR $v_{max}$(KBr): 3392, 1699, 1664, 1646, 1597, 1553 cm$^{-1}$.

NMR (DMSO-d₆)δ: 0.80–1.04 (8H, m), 1.86 (3H, s), 2.15 (2H, m), 4.85 (2H, d, J=18.0Hz), 4.99 (2H, d, J=7.8 Hz), 4.99 (1H, d, J=18.0 Hz), 6.91 (1H, d, J=7.8 Hz), 7.27–7.53 (8H, m), 7.99 (1H, s), 9.49 (1H, s).

Elemental Analysis (for $C_{28}H_{29}N_5O_8S \cdot 1.7H_2O$)

Calcd.: C, 53.70; H, 5.21; N, 11.18; S, 5.12

Found: C, 53.59; H, 5.08; N, 11.37; S, 5.30.

EXAMPLE 52

1,5-Bis-(cyclopropylcarbonylmethyl)-3-(N'-(m-(carbomethoxymethyl)phenyl)ureido)-1H-1,5-benzodiazepine-2,4(3H,5H)-dione 17-xii 1) 3-(N'-(m-(carbomethoxymethyl)phenyl)ureido)-1H-1,5-benzodiazepine-2,4(3H,5H)-dione The titled compound is prepared in a manner similar to that described above using m-carbomethoxymethyl)phenylisocyanate and amine 4 in 86.8% yield.

M.p.>300° C.

IR $v_{max}$(KBr): 3372, 1717, 1678, 1607, 1600, 1559, 1501 cm$^{-1}$.

NMR (DMSO-d₆)δ: 3.60 (5H, s), 4.63 (1H, d, J=7.4 Hz), 6.80 (1H, d, J=6.6 Hz), 6.84 (1H, d, J=7.4 Hz), 7.11–7.31 (7H, m), 9.14 (1H, s), 10.77 (2H, s).

Elemental Analysis (for $C_{19}H_{18}N_4O_5 \cdot 0.3H_2O$)

Calcd.: C, 58.58; H, 4.83; N, 14.45

Found: C, 58.70; H, 4.92; N, 14.56.

2) The titled Compound 17-xii is prepared by the N-alkylation carried out in a manner similar to that described in Examples above. Yield, 92.3%; m.p.= 199°–202° C.

IR $v_{max}$ (KBr): 3382, 1699, 1613, 1597, 1558 cm$^{-1}$.

NMR (CDCl₃) δ: 0.97 (4H, m), 1.10 (4H, m), 2.00 (2H, m), 3.54 (2H, s), 3.66 (3H, s), 4.79 (2H, d, J=18.0Hz), 4.91 (2H, d, J=18.0 Hz), 5.33 (1H, d, J=7.4 Hz), 6.42 (1H, d, J=7.8 Hz), 6.89 (1H, dt, J=2.0, 6.2 Hz), 7.10–7.36 (8H, m).

Elemental Analysis (for $C_{29}H_{30}N_4O_7$)

Calcd.: C, 63.73; H, 5.53; N, 10.25

Found: C, 63.54; H, 5.62; N, 10.07.

EXAMPLE 53

1,5-Bis-(cyclopropylcarbonylmethyl)-3-(N'-(m-(carbomethyl)phenyl)ureido)-1H-1,5-benzodiazepine-2,4(3H,5H)-dione 17-xiii Yield, 59.3%; m.p.=209°–211° C.

IR $v_{max}$ (KBr): 3385, 1700, 1665, 1647, 1616, 1597, 1588, 1501 cm$^{-1}$.

NMR (DMSO-d$_6$)δ: 0.80–1.08 (8H, m), 2.15 (2H, qui, J=6.1 Hz), 3.47 (2H, s), 4.84 (2H, d, J=18.0Hz), 4.98 (2H, d, J=18.0Hz), 4.99 (1H, d, J=8.0Hz), 6.80 (1H, dt, J=2.0, 6.8 Hz), 6.85 (1H, d, J=8.0 Hz), 7.09–7.47 (7H,m), 9.12 (1H, s), 12.30 (1H, br.s).

Elemental Analysis (for C$_{28}$H$_{28}$N$_4$O$_7$)

Calcd.: C, 62.31; H, 5.38; N, 10.38

Found: C, 62.59; H, 5.47; N, 10.10.

EXAMPLE 54

1,5-Bis-(cyclopropylcarbonylmethyl)-3-(N'-(p-(carbomethoxy)phenyl)ureido)-1H-1,5-benzodiazepine-2,4(3H,5H)-dione 17-xiv Compound 17-xiv is prepared using, as a starting material, 4-methoxyphenylisocyanate obtained from the previously prepared amine 16 h and methyl 4-aminobenzoate.

M.p.=278°–279° C.

IR $v_{max}$ (KBr): 3350, 1721, 1680, 1650, 1600, 1539, 1500, 1435 cm$^{-1}$.

NMR (DMSO-d$_6$)δ: 0.78–1.04 (8H, m), 2.06–2.22 (2H, m), 3.79 (3H, s), 4.83 (2H, d, J=18.4 Hz), 4.99 (2H, d, J=8.0Hz), 5.00 (2H, d, J=18.4 Hz), 7.03 (1H, d, J=7.6 Hz), 7.27–7.53 (4H, m), 7.45 (2H, d, J=8.6 Hz), 7.83 (2H, d, J=8.6 Hz), 9.54 (1H, s).

Elemental Analysis (for C$_{28}$H$_{28}$N$_4$O$_7$·0.4H$_2$O)

Calcd.: C, 62.31; H, 5.38; N, 10.38

Found: C, 62.23; H, 5.27; N, 10.40.

EXAMPLE 55

1,5-Bis-(cyclopropylcarbonylmethyl)-3-(N'-(p-(carboxy)phenyl)ureido)-1H-1,5-benzodiazepine-2,4(3H,5H)-dione 17-xv Compound 17-xv is prepared by hydrolyzing the ester 17xiv with an alkali in a conventional manner.

M.p.=261°–262° C.

IR $v_{max}$ (KBr): 3400, 1695, 1600, 1545, 1503, 1432 cm$^{-1}$.

NMR (DMSO-d$_6$)δ: 0.78–1.05 (8H, m), 2.04–2.23 (2H, m), 4.83 (2H, d, J=18.4 Hz), 5.00 (1H, d, J=7.8 Hz), 5.00 (2H, d, J=18.4 Hz), 7.00 (1H, d, J=7.8 Hz), 7.26–7.51(4H, m), 7.43 (2H, d, J=8.8 Hz), 7.81 (2H, d, J=8.8 Hz), 9.49 (1H, s).

Elemental Analysis (for C$_{27}$H$_{26}$N$_4$O$_7$·0.3H$_2$O)

Calcd.: C, 61.19; H, 5.12; N, 10.69

Found: C, 61.85; H, 5.07; N, 10.73.

EXAMPLE 56

1,5-Bis-(cyclopropylcarbonylmethyl)-3-(N'-(p-cyanophenyl)ureido)-1H-1,5-benzodiazepine-2,4(3H,5H)-dione 17-xvi Compound 17-xvi is prepared using, as a starting material, 4-cyanophenylisocyanate obtained from the previously prepared amine 16 h and 4-cyanoaniline.

M.p.=260°–262° C.

IR $v_{max}$ (KBr): 3380, 2220, 1703, 1670, 1600, 1540, 1500, 1430 cm$^{-1}$.

NMR (DMSO-d$_6$)δ: 0.76–1.05 (8H, m), 2.06–2.24 (2H, m), 4.83 (2H, d, J=18.2 Hz), 4.99 (1H, d, J=7.6 Hz), 5.00 (2H, d, J=18.2 Hz), 7.05 (1H, d, J=8.0 Hz), 7.24–7.63 (4H m), 7.50 (2H, d,J=8.8 Hz), 7.68 (2H, d, J=8.8 Hz), 9.64 (1H, s).

Elemental Analysis (for C$_{27}$H$_{25}$N$_5$O$_5$·0.4H$_2$O)

Calcd.:C, 64.00; H, 5.13; N, 13.82

Found: C, 64.07; H, 5.17;N, 13.65.

EXAMPLE 57

1,5-Bis-(cyclopropylcarbonylmethyl)-3-(N'-(m-(tetrazol-4-ylmethylthio)phenyl)ureido)-1H-1,5-benzodiazepine-2,4(3H,5H)-dione 17-xvii 1) 3-(Tetrazo-5-yl)methylaniline trifluoroacetate The titled compound is prepared by treating m-aminobenzenethiol in a manner similar to that described above in connection with the preparation of 3-(tetrazo-5-yl) methoxyaniline.

NMR(DMSO-d$_6$)δ: 4.53 (2H, s), 6.72–7.02 (3H, m), 7.10–7.28 (1H, m).

2) Compound 17-xvii is prepared in a manner similar to that described in Example 41 for the preparation of Compound 17i using 3-(tetrazo-5-yl)methylaniline trifluoroacetate prepared above 1) and the previously prepared amine 16 h.

M.p.=214°–220° C.

NMR (DMSO-d$_6$)δ: 0.79–1.02 (8H, m), 2.03–2.23 (2H, m), 4.33 (2H, s), 4.83 (2H, d, J=18.0 Hz), 4.99 (1H, d, J=8.0 Hz), 5.00 (2H, d, J=18.0 Hz), 6.87–7.00 (2H, m), 7.00–7.18 (2H, m), 7.27–7.46 (5H, m), 9.18 (1H, s).

EXAMPLE 58

1,5-Bis-(pyrrolidinocarbonylmethyl)-3-(N'-(m-(carboethoxy)phenyl)ureido)-1H-1,5-benzodiazepine-2,4(3H,5H)-dione 18-i Compound 18-i is prepared using, as a starting material, 3-ethoxycarbonylphenylisocyanate obtained from the previously prepared amine 16a and ethyl 3-aminobenzoate.

NMR (DMSO-d$_6$)δ: 1.30 (3H, t, J=6.8 Hz), 1.69 2.00 (8H, m), 3.23–3.52 (8H, m), 4.29 (2H, q, J=6.8 Hz), 4.49 (2H, d, J=17.2 Hz), 4.72 (2H, d, J=17.2 Hz), 5.00 (1H, d, J=8.0Hz), 6.87 (1H, d, J=8.0Hz), 7.31–7.60 (7H, m), 8.07 (1H, s), 9.49 (1H, s).

Elemental Analysis (for C$_{43}$H$_{53}$N$_7$O$_6$·0.5H$_2$O)

Calcd.: C, 65.46; H, 6.96; N, 12.43

Found: C, 65.40; H, 6.91; N, 12.44.

EXAMPLE 59

1,5-Bis-(pyrrolidinocarbonylmethyl)-3-(N'-(m-(tetrazolylphenyl)ureido)-1H-1,5-benzodiazepine-2,4(3H,5H)-dione 18-iv Compound 18-iv is prepared using, as a starting material, 3-(1H-tetrazol-5-yl)phenylisocyanate obtained from the previously prepared amine 16a and 3-amino-(1H-tetrazol-5-yl) benzene (a compound disclosed in EP 0 508 796 A1).

M.p.=290°–293° C.

IR $v_{max}$ (KBr): 3425, 1705, 1642, 1570, 1507, 1455 cm$^{-1}$.

NMR (DMSO-d$_6$)δ: 1.64–1.98 (8H, m), 3.23–3.38 (4H, m), 3.42 (4H, m) 4.51 (2H, d, J=17.4 Hz), 4.72 (2H, d, J=17.4 Hz), 5.02 (1H, d, J=8.2 Hz), 6.81 (1H, d, J=8.2 Hz), 7.19 (1H, d, J=8.2 Hz), 7.35–7.61 (7H, m), 7.82 (1H, s), 9.18 (1H, s).

37

Elemental Analysis (for $C_{21}H_{27}N_5O_4 \cdot 0.7H_2O$)
Calcd.: C, 59.20; H, 6.72; N, 16.44
Found: C, 59.38; H, 6.46; N, 16.20.

EXAMPLE 60

1,5-Bis-(pyrrolidinocarbonylmethyl)-3-(N'-(m-(carbomethoxymethyl)phenyl)ureido)-1H-1,5-benzodiazepine-2,4(3H,5H)-dione 18-xii The titled Compound 18-xii is prepared in a manner similar to that used for the preparation of Compound 17-xii.

IR $v_{max}$ (KBr): 3425, 1735, 1691, 1652 cm$_{-1}$.

NMR (CDCl$_3$) δ: 1.84 (4H, qui, J=6.2 Hz), 1.97 (4H, qui, J=6.2 Hz), 3.36–3.58 (10H, m), 3.67 (3H, s) 4.61 (4H, s), 5.24 (1H, d, J=7.0 Hz), 6.44 (1H, d, J=7.4 Hz), 6.87 (1H, dt, J=1.3, 7.4 Hz), 7.13(1H, m), 7.20–7.30 (2H, m), 7.30 (2H, m), 7.39 (1H, s), 7.52 (2H, m).

Elemental Analysis (for $C_{31}H_{36}N_6O_7 \cdot 9H_2O$)
Calcd.: C, 59.97; H, 6.14; N, 13.54
Found: C, 59.96; H, 6.17; N, 13.54.

EXAMPLE 61

1,5-Bis-(pyrrolidinocarbonylmethyl)-3-(N'-(m-(carboxymethyl)phenyl)ureido)-1H-1,5-benzodiazepine-2,4(3H,5H)-dione 18-xiii The titled Compound 18-xiii is prepared by hydrolyzing the compound prepared in Example 60 in a conventional manner.

M.p.=228°–230° C.

IR $v_{max}$ (KBr): 3435, 3389, 1705, 1639, 1566 cm$^{-1}$.

NMR(CD$_3$OD)δ: 1.81–2.09 (8H, m), 3.44 (4H, t, J=6.7 Hz), 3.52 (2H, s) 3.56 (4H, m), 4.66 (2H, d, J=16.8 Hz), 4.76 (2H, d, J=16.8 Hz), 5.19 (1H, s), 6.89 (1H, d, J=7.4 Hz), 7.17 (1H, d, J=7.4, 9.0 Hz), 7.23–7.31 (2H, m), 7.41 (2H, m), 7.58 (2H, m).

Elemental Analysis (for $C_{30}H_{34}N_6O_7 \cdot 0.7H_2O$)
Calcd.: C, 59.73; H, 5.91; N, 13.93
Found: C, 59.60; H, 5.82; N, 13.97.

Example 62

1,5-Bis-(cyclopropylmethyl)-3-(N'-(m-tetrazolylphenyl)ureido)-1H-1,5-benzodiazepine-2,4(3H,5H)-dione 19-iv Compound 19-iv is prepared using, as a starting material, 3-(1H-tetrazol-5-yl)phenylisocyanate obtained from the previously prepared amine 16o and 3-amino-(1H-tetrazol-5-yl) benzene (a compound disclosed in EP 0 508 796 A1).

M.p.=228°–230° C.

IR $v_{max}$ (KBr): 3380, 1688, 1654, 1600, 1575,1543, 1500, 1425 cm$^{-1}$.

NMR (DMSO-d$_6$)δ: 0.03–0.22 (4H, m), 0.22–0.39 (4H, m), 0.71–0.92 (2H, m), 3.67 (2H, dd, J=15.8 & 7.0Hz), 4.17 (2H, dd, J=15.8 & 7.0 Hz), 4.83 (1H, d, J=7.8 Hz), 6.94 (1H, d, J=7.8 Hz), 7.38–7.50 (4H, m), 7.52–7.59 (1H, m), 7.66–7.78 (2H, m)), 8.15 (1H, s), 9.43 (1H, s).

Elemental Analysis (for $C_{25}H_{26}N_8O_3 \cdot 1.7H_2O$)
Calcd.: C, 58.06; H, 5.73; N, 21.67
Found: C, 58.30; H, 5.44; N, 21.35

EXAMPLE 63

1,5-Bis-(thienylcarbonylmethyl)-3-(N'-(m-tetrazolylphenyl)ureido)-1H-1,5-benzodiazepine-2,4(3H,5H)-dione 20-iv Compound 20-iv is prepared using, as a starting material, 3-(1H-tetrazol-5-yl)phenylisocyanate obtained from the previously prepared amine 16g and 3-amino-(1H-tetrazol-5-yl) benzene (a compound disclosed in EP 0 508 796 A1).

M.p.=243°–244° C.

IR $v_{max}$ (KBr): 3390, 1705, 1663, 1573, 1502,1408, 1240 cm$^{-1}$.

NMR (DMSO-d$_6$)δ: 5.15 (1H, d, J=8.0Hz), 5.30 (2H, d, J=17.8 Hz), 5.55 (2H, d, J=17.8 Hz), 6.93 (1H, d, J=8.0Hz), 7.27–7.60 (9H, m), 8.01 (1H, s), 8.06–8.20 (4H, m), 9.29 (1H, s).

Elemental Analysis (for $C_{43}H_{53}N_7O_6 \cdot 0.5H_2O$)
Calcd.: C, 65.46; H, 6.96; N, 12.43
Found: C, 65.40; H, 6.91; N, 12.44.

EXAMPLE 64

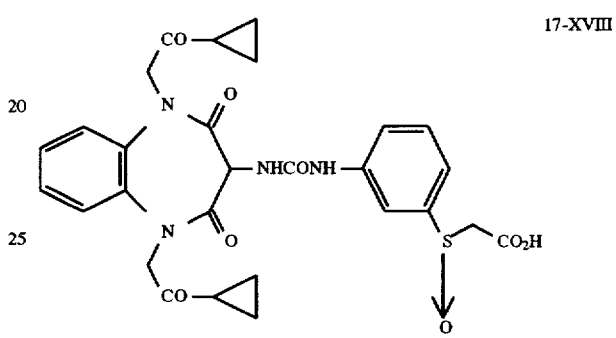

17-XVIII

To a solution of Compound 17-ix (318 mg, 0.56 mmol) prepared in Example 49 in dichloromethane (12 ml) and methanol (3 ml) is added 80% m-chloroperbenzoic acid (122 mg, 0.56 mmol) at –5° C. and the mixture is stirred for another 1 hr. To the reaction mixture is added 5% aqueous sodium thiosulfate solution and the mixture is extracted with dichloromethane. The organic layer is washed with water, dried over sodium sulfate and concentrated under reduced pressure. The resultant crystalline residue is crystallized from dichloromethane-ether to obtain the titled Compound 17-xix (140 mg; yield, 43%) as white crystals.

M.p.=216°–217° C.

NMR (CDCl$_3$+CD$_3$ODδ: 0.96–1.18(8H,m), 1.94–2.10 (2H,m), 3.65 (1H, d, J=14 Hz) 3.83 (1H, d, J=14 Hz), 3.83 (1H, d, J=14 Hz), 4.79 (2H, d.d, J=18 & 2.6 Hz), 4.95 (2H, d, J=18 Hz) 7.22- 7.36 (7H, m), 7.67, (1H.S).

EXAMPLE 65

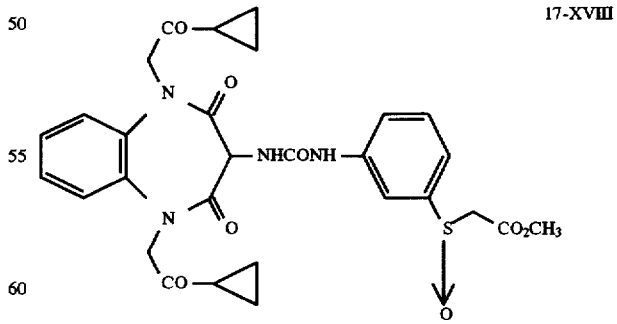

17-XVIII

The S-oxide (250 mg, 0.43 mmol) obtained according to the method above is treated with a solution of excessive diazomethane in ether. The resultant crude product, when purified by chromatography on silica gel (ethyl acetate/ methanol (100:0.5)) and crystallized from dichloromethane-ether, gives the titled Compound 17-xix (200 mg; yield, 78%) as white crystals.

M.p.=208°–210° C.

NMR(CDCl$_3$+CD$_3$OD)δ: 0.95–1.18 (8H, m), 1.88–2.08 (2H,m), 3.68 (1H, d, J=14 Hz), 3.71 (3H, S), 3.82 (1H, d, J=14 Hz), 4.79 (2H, d.d, J=11.4 & 6.6 Hz), 4.96 (2H, d, d, J=14.8 & 3.2 Hz), 5.31 (1H, d, J=7.4 Hz), 6.71 (1H, d, J=7.4 Hz), 7.13–7.43 (6H,m), 7.52 (1H, d, J=9.4 Hz), 7.62 (1H,S), 8.43(1H,S).

A hybrid-type compound was prepared by coupling a compound (I) of the present invention prepared in Examples above with an H$_2$B.

NMR (CDCl$_3$+CD$_3$OD)δ: 0.44 (4H, m), 0.65 (4H, m), 1.48 (2H, m), 1.66 (4H,m), 1.80 (2H, m), 1.96 (2H, m), 2.40–2.70 (6H, m), 3.16 (2H, t, J=6.5 Hz),3.38 (2H, m), 3.60 (2H, br.s), 4.02 (2H, t, J=6.2 Hz), 4.33 (2H, d, J=16.2 Hz), 4.71 (2H, d, J=16.2 Hz), 5.00 (2H, s), 5.11 (1H, s), 6.81 (1H, dd,J=7.9, 1.7 Hz), 6.89(2H, m), 6.99 (1H, s), 7.13–7.31 (4H, m), 7.37 (4H,s).

Elemental Analysis(For C$_{47}$H$_{59}$N$_9$O$_9$·1.2H$_2$O)

Found: C, 61.63; H, 6.71; N, 13.76

Calcd.: C, 61.65; H, 6.76; N, 13.77.

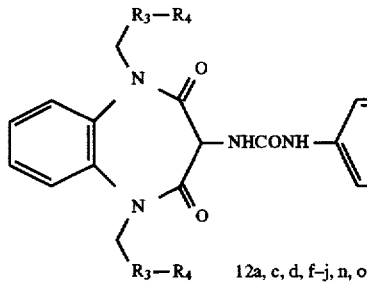 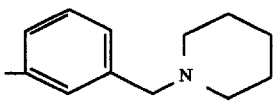

12a, c, d, f–j, n, o

Reference Example 1

1,5-Bis-(pyrrolidinecarbonylmethyl)-3-(N'-(3-(3-(3-(3-(pyrrolidinomethyl)phenoxy)propylcarbamoyl) propylcarbamoyloxymethyl)phenyl)ureido)-1H-1,5-benzodiazepine-2,4(3H,5H)-dione 12a A solution of Compound 11a (224 mg, 0.324 mmol) prepared in Example 34, N,N-dimethylaminopropyl-N'-ethylcarbodiimide 2HCl (138 mg, 0.720 mmcl) and 1-hydroxybenzotriazole (54 mg, 0.355 mmol) in dimethylformamide (10 ml) is stirred for 30 min under ice-cooling. To the mixture are added a solution of 3-((3-piperidinomethyl)phenoxy)propylamine (130 mg, 0.523 mmol) in dimethylformamide (2 ml) and triethylamine (0.2 ml). The mixture is stirred for 16 hr at room temperature and distilled under the reduced pressure to remove the solvent. The resultant residue is purified by chromatography on silica gel (42 g gel, CHCl$_3$/MeOH (9:1)) to obtain Compound 12a (198 mg, 66.2%).

IR ν$_{max}$ (KBr): 3416, 1707, 1652, 1559 cm$^{-1}$.

NMR (CDCl$_3$) δ: 1.44 (2H, m), 1.62 (4H, m), 1.70–2.04 (12H, m), 2.21 (2H, t, J=6.6 Hz), 2.50 (4H, br.s), 3.17 (2H, m), 3.24–3.50 (1OH, m), 3.55 (2H, s), 3.98 (2H, t, J=5.8 Hz), 4.53 (2H, d, J=16.4 Hz), 4.62 (2H, d, J=16.4 Hz), 4.93 (2H, s), 5.19 (1H, d, J=7.0 Hz), 6.07 (1H, m), 6.63–6.91 (4H, m), 6.96–7.40 (8H, m), 7.47 (2H, m), 8.44 (1H, s).

Elemental Analysis (for C$_{49}$H$_{63}$N$_9$O$_9$·1.5H$_2$O)

Found: C, 62.05; H, 6.93; N, 13.31

Calcd.: C, 62.01; H, 7.01; N, 13.28.

Compounds described in the following Reference Examples are prepared in a manner similar to that described in Reference Example 1.

Reference Example 2

1,5-Bis-(cyclopropylcarbamoylmethyl)-3-(N'-(3-(3-(3-(3-(pyrrolidinomethyl)phenoxy)propylcarbamoyl) propylcarbamoyloxymethyl)phenyl)ureido)-1H-1,5-benzodiazepine-2,4(3H,5H)-dione 12c IR ν$_{max}$ (KBr): 3360, 3316,1708, 1665, 1599, 1556 cm$^{-1}$.

Reference Example 3

1,5-Bis-(o-methylphenacyl)-3-(N'-(3-(3-(3-(3-piperidinomethyl)phenoxy)propylcarbamoyl)-propylcarbamoyloxymethyl)phenyl)ureido)-1H-1,5-benzodiazepine-2,4(3H,5H)-dione 12d M.p.=132°–133° C.

IR ν$_{max}$ (nujol): 3347, 1702, 1690, 1668, 1612, 1568 cm$_1$.

NMR (DMSO-d$_6$) δ: 1.31–1.55 (6H, m), 1.61 (2H, quintet, J=7.0 Hz), 1.81 (2H, quintet, J=6.0Hz), 2.06 (2H, t, J=7.8 Hz), 2.26–2.39 (4H, m), 2.36 (6H,s), 2.97 (2H, q, J=6.0Hz), 3.18 (2H, q, J=6.0 Hz), 3.34 (2H,s), 3.94 (2H, t, J=6.4 Hz), 4.92 (2H, s), 5.07 (1H, d, J=8.0Hz), 5.09 (2H, d, J=17.6 Hz), 5.20 (2H, d, J=17.6 Hz), 6.71–7.00 (5H, m), 7.12–7.58 (15H, m), 7.73–7.95 (3H, m), 9.16 (1H, s).

Elemental Analysis (for C$_{55}$H$_{61}$N$_7$O$_9$·0.5H$_2$O)

Found: C, 67.90; H, 6.35; N, 10.05

Calcd.: C, 67.88; H, 6.42; N, 10.08.

Reference Example 4

1,5-Bis-(2-furylcarbonylmethyl)-3-(N'-(3-(3-(3-piperidinomethyl)phenoxy)propylcarbamoyl)-propylcarbamoyloxymethyl)phenyl)ureido)-1H-1,5-benzodiazepine-2,4(3H,5H)-dione 12f M.p.=140°–145° C.

IR ν$_{max}$ (nujol): 1705, 1691, 1639, 1598, 1571 cm$_{-1}$.

NMR (DMSO-d$_6$)δ: 1.31–1.55 (6H, m), 1.61 (2H, quintet, J=7.0Hz),1.81 (2H, quintet, J=6.0Hz), 2.06 (2H, t, J=7.8 Hz), 2.26–2.39 (4H, m), 2.97 (2H, q, J=6.0Hz), 3.18 (2H, q, J=6.0 Hz),3.34 (2H, t, J=6.0Hz), 4.92 (2H, s), 5.11 (1H,d, J=8.0Hz), 5.12 (2H, d, J=8.0Hz), 5.38 (2H, d, J=18.0Hz), 6.80 (2H, d.d, J=3.6 & 1.8 Hz), 6.80–6.93 (5H, m), 7.13- 7.54 (9H, m), 7.65 (2H, d.d, J=3.6 & 0.6 Hz), 7.88 (1H, t, J=5.8 Hz), 8.10 (2H, d.d, J=1.8 & 0.6 Hz), 9.18 (1H, s).

Elemental Analysis (for $C_{49}H_{53}N_7O_{11} \cdot H_2O$)
Found: C, 63.06; H, 5.83; N, 10.56
Calcd.: C, 63.01; H, 5.94; N, 10.50.

Reference Example 5

1,5-Bis-(2-thienylcarbonylmethyl)-3-(N'-(3-(3-(3-(3-(piperidinomethyl)phenoxy)propylcarbamoyl)-propylcarbamoyloxymethyl)phenyl)ureido)-1H-1,5-benzodiazepine-2,4(3H,5H)-dione 12g M.p.=165°–167° C.
IR $v_{max}$ (nujol): 3338, 1704, 1666, 1636, 1567 cm$^{-1}$.
NMR (DMSO-d6) δ: 1.31–1.55 (6H, m), 1.61 (2H, quintet, J=7.0Hz),1.81 (2H, quintet, J=6.0Hz), 2.06 (2H, t, J=7.8 Hz), 2.26–2.39 (4H, m), 2.97 (2H, q, J=6.0Hz), 3.18 (2H, q, J=6.0Hz),d.34 (2H, s), 3.94 (2H, t, J=6.0Hz), 4.92 (2H, s), 5.12 (1H,d, J=8.0 Hz), 5.29 (2H, d, J=18.1 Hz), 5.54 (2H, d, J=18.1 Hz), 6.70–6.97 (5H, m), 7.15–7.39 (7H, m), 7.40–7.50 (4H, m), 7.88 (1H, t, J=6.0 Hz), 8.07–8.18 (4H, m), 9.18 (1H, s).
Elemental Analysis (for $C_{49}H_{53}N_7O_9S_2 \cdot 0.8H_2O$)
Found: C, 61.14; H, 5.80; N, 10.38
Calcd.: C, 61.14; H, 5.72; N, 10.19; S, 6.66.

Reference Example 6

1,5-Bis-(cyclopropylcarbonylmethyl)-3-(N'- (3-(3-(3-(3-(piperidinomethyl)phenoxy)propylcarbamoyl)-propylcarbamoyloxymethyl)phenyl)ureido)-1H-1,5-benzodiazepine-2,4(3H,5H)-dione 12 h Yield, 71.6%.
IR $v_{max}$ (KBr): 3357, 1701, 1598, 1559, 1502 cm$^{-1}$.
NMR (CDCl$_3$)δ: 0.95 (4H, m), 1.06 (4H, in), 1.57 (4H, m), 1.70–2.05 (6H, m), 2.18 (2H, t, J=6.8 Hz), 2.42 (4H, br.s), 3.17 (2H, qui, J=5.4 Hz), 3.36 (2H, q, J=6.0 Hz), 3.47 (2H, s), 3.96 (2H, t, J=5.8 Hz), 4.75 (2H, d,J=18.0 Hz), 4.89 (2H, d, J=18.0 Hz), 4.95 (2H, s), 5.31 (1H, d, J=7.6 Hz), 5.71 (1H, t, J=5.3 Hz), 6.68–6.79 (6H, m), 7.03–7.35 (8H, m), 8.06 (1H, s).
Elemental Analysis (for $C_{47}H_{57}N_7O_9 \cdot 0.7H_2O$)
Found: C, 64.41; H, 6.78; N, 11.32
Calcd.: C, 64.40; H, 6.71; N, 11.18.

Reference Example 7

1,5-Bis-(cyclopentylcarbonylmethyl)-3-(N'-(3-(3-(3-(3-(piperidinomethyl)phenoxy)propylcarbamoyl)-propylcarbamoyloxymethyl)phenyl)ureido)-1H-1,5-benzodiazepine-2,4(3H,5H)-dione 12i Yield, 68.5%.
IR $v_{max}$ (KBr): 3398, 1702, 1670, 1646, 1614, 1599, 1501 cm$^{-1}$.
NMR (CDCl$_3$)δ: 1.35–2.00 (26H, m), 2.20 (2H, t, J=6.6 Hz), 2.45 (4H, br.s), 2.91 (2H, qui, J=7.9 Hz), 3.18 (2H, q, J=5.7 Hz), 3.36 (2H, q, J=6.0 Hz), 3.50 (2H, s), 3.96 (2H, t, J=5.8 Hz), 4.66 (2H, d, J=18.0Hz), 4.76 (2H, d, J=18.0Hz), 4.96 (2H, s), 5.28 (1H, d, J=7.0Hz), 5.71 (1H, t, J=6.0Hz), 6.65 (1H, d, J=7.6 Hz), 6.61–6.90 (4H, m), 6.97 (1H, s), 7.06–7.39 (8H, m), 8.06 (1H, s).

Elemental Analysis (for $C_{51}H_{65}N_7O_9 \cdot H_2O$)
Found: C, 65.23; H, 7.14; N, 10.59
Calcd.: C, 65.30; H, 7.20; N, 10.45.

Reference Example 8

1,5-Bis-(1-methylimidazol-2-ylmethyl)-3-(N'-(3-(3-(3-(3-(piperidinomethyl)phenoxy)-propylcarbamoyl) propylcarbamoyloxymethyl)phenyl)ureido)- 1H-1,5-benzodiazepine-2,4(3H,5H)-dione 12j Yield, 77.1%.
NMR (CDCl$_3$)δ: 1.44 (2H, m), 1.58 (4H, m), 1.78 (2H, m), 1.91 (2H, m), 2.17 (2H, t, J=6.6 Hz), 2.42 (4H, br.s), 3.15 (2H, qui, J=5.8 Hz), 3.36 (2H, q, J=6.2 Hz), 3.48 (2H, s), 3.50 (6H, s), 3.96 (2H, t, J=5.8 Hz), 4.94 (2H, s), 4.98 (4H, s), 5.14 (1H, d, J=7.4 Hz), 5.77 (1H, t, J=6.4 Hz), 6.65–6.98 (6H, m), 6.73 (2H, d, J=1.2 Hz), 6.88 (2H, d, J=1.2 Hz), 7.04–7.25 (4H, m), 7.30 (2H, m), 7.77 (2H, m), 8.42 (1H, s).
Elemental Analysis (for $C_{47}H_{57}N_{11}O_7 \cdot 13H_2O$)
Found: C, 61.93; H, 6.64; N, 17.13
Calcd.: C, 61.94; H, 6.59; N, 16.90.

Reference Example 9

1,5-Bis-allyl-3-(N'-(3-(3-(3-(3-(piperidinomethyl) phenoxy)propylcarbamoyl) propylcarbamoyloxymethyl)phenyl)ureido)-1H-1,5-benzodiazepine-2,4(3H,5H)-dione 12n.

Amorphous solid.
IR $v_{max}$ (nujol): 3308, 1697, 1665, 1638, 1614, 1565 cm$^{-1}$.
NMR (DMSO-d$_6$)δ: 1.31–1.55 (6H, m), 1.61 (2H, quintet, J=7.0Hz), 1.81 (2H,quintet, J=6.0 Hz), 2.06 (2H, t, J=7.8 Hz), 2.26–2.39 (4H, m), 2.97 (2H, q, J=6.0 Hz), 3.18 (2H, q, J=6.0Hz), 3.34 (2H,s), 3.94 (2H, t, J=6.4 Hz), 4.45 (2H, d,d, J=16.0 & 5.8 Hz), 4.67 (2H, d.d, J=16.0 & 5.8 Hz), 4.90 (1H, d, J=7.4 Hz), 4.92 (2H, s),5.08 (2H, s), 5.14 (2H, d, J=3.6 Hz), 5.59–5.81 (2H, m), 6.72–6.95 (5H, m), 7.12–7.30 (4H, m), 7.35 (1H, s), 7.36–7.48 (2H, m), 7.55–7.68 (2H, m), 7.87 (1H, t, J=5.4 Hz), 9.21 (1H, s).
Elemental Analysis (for $C_{43}H_{53}N_7O_6 \cdot 0.5H_2O$)
Found: C, 65.40; H, 6.91; N, 12.44
Calcd.: C, 65.46; H, 6.96; N, 12.43.

Reference Example 10

1,5-Bis-(cyclopropylmethyl)-3-(N,-(3-(3-(3-(3-(piperidinomethyl)phenoxy)propylcarbamoyl)-propylcarbamoyloxymethyl)phenyl)ureido)-1H-1,5-benzodiazepine-2,4(3H,5H)-dione 12o Amorphous solid.
IR $v_{max}$ (nujol): 3383, 3297, 1686, 1658, 1637, 1604, 1569 cm$^{-1}$.
NMR (DMSO-d$_6$)δ: 0.09–0.18 (4H, m), 0.23–0.37 (4H, m), 0.72–0.92 (2H, m), 1.31–1.55 (6H, m), 1.61 (2H, qui, J=7.0Hz), 1.81 (2H, quintet, J=6.0Hz), 2.06 (2H, t, J=7.8 Hz), 2.24–2.33 (4H, m), 2.97 (2H, q, J=6.0Hz), 3.18 (2H, q, J=6.0Hz), 3.34 (2H,s), 3.66 (2H, d.d, J=14.0 & 7.0 Hz), 3.94 (2H, t, J=6.0 Hz), 4.16 (2H, d.d, J=14.0 & 7.0 Hz), 4.79 (1H, d, J=7.4 Hz), 4.91 (2H, s), 6.72–6.91 (5H, m), 7.12–7.29 (4H, m), 7.36 (1H, s), 7.38–7.49 (2H, m), 7.67–7.78 (2H, m), 7.86 (1H, t, J=5.6 Hz), 9.21 (1H, s).

Elemental Analysis (for $C_{45}H_{57}N_7O_7$)

Found: C, 66.87; H, 7.14; N, 12.08

Calcd.: C, 66.89; H, 7.11; N, 12.13.

Reference Example 11

1,5-Bis-(tert-butyloxycarbonyl-methyl)-3-(N'-(3-(3-(3-(3-(piperidinomethyl)phenoxy)-propylcarbamoyl) propylcarbamoyloxymethyl)phenyl)ureido)-1H-1,5-benzodiazepine-2,4(3H,5H)-dione 12s Yield, 64.1%.

IR $v_{max}$(KBr): 3381, 1741, 1711, 1677, 1646, 1614, 1599, 1560 cm$^{-1}$.

NMR (CDCl$_3$)δ: 1.43 (20H, m), 1.59 (4H, m), 1.73–2.00 (4H, m), 2.19 (2H, t, J=7.0Hz), 2.45 (4H, br.s), 3.20 (2H, qui, J=5.8 Hz), 3.35 (2H, q, J=6.1 Hz), 3.50 (2H, s), 3.97 (2H, t, J=6.0Hz), 4.38 (2H, d J=17.6 Hz), 4.52 (2H, d, J=17.6 Hz), 4.95 (2H, s), 5.08 (1H, br.s), 5.31 (1H, d, J=7.6 Hz), 5.60 (1H, t, J=6.0Hz), 6.70–7.23 (9H, m), 7.36 (4H, s), 7.89 (1H, s).

Elemental Analysis (for $C_{49}H_{65}N_7O_{11} \cdot 0.8H_2O$)

Found: C, 62.38; H, 7.08; N, 10.50

Calcd.: C, 62.44; H, 7.12; N, 10.40.

Compounds of the formula (I) of the present invention prepared in Examples were subjected to in vitro and in vivo tests for evaluating the antagonistic activity gastrin receptor and/or CCK-B receptor.

Experiment 1 In Vivo Test

Evaluation of Inhibitory Effect on Gastric Acid Secretion by Schild Method

Twenty four hour starved (ad libitum for water) male Sprague Dawley rats (8-week-old) were anesthetized with urethane (1.5 g/kg S.C.) and kept breathing with esophagus cannulas. After laparotomy, esophagus cannulas were inserted orally up to proventriculus and ligated around gastric cardiac. Perfusion cannulas were inserted from duodenum into stomach and ligated around pylorus. Another cannulas were placed into duodenum and ligated for administration of drug. After sutra of abdomen, stomach was perfused via the esophagus cannulas with physiological saline (37° C.) while collecting perfusate for a 15 min interval. The perfusate was subjected to titration with 0.001 N NaOH solution to determine the acidity. When the basal acid secretion became stable, pentagastrin (10 μl/kg/hr) was administered in a sustained manner via common carotid vein for about 90 min until the acid secretion reached approximately the highest level, when a test compound (0.5% M.C. suspension) was administered into duodenum through cannulas. The perfusate was collected for a 15 min interval to monitor the acid secretion for 90 min. The percent inhibition was calculated as follows:

Percent inhibition (%)=100×(A–B)/(C–B)

A: the minimum value of total acidity observed after the administration of a test compound;

B: the total acidity obtained immediately before the administration of pentagastrin; and C: the total acidity obtained immediately before the administration of a test compound.

Results are summarized in Table 1 below.

Experiment 2 In Vitro Test for Evaluation of Gastrin and/or CCK-B Antagonism The pharmacological effect of compounds (I) prepared in Examples above were evaluated in vitro with respect to antagonistic activity against gastrin receptor, CCK-B receptor or CCK-A receptor, using fundic gland cells of guinea pig, crude membrane specimen from mouse cerebral cortex, or crude membrane specimen from mouse pancreas, respectively.

Animals used in test

Male Hartley guinea pig (450–600 g) or male ddY mouse (24–30 g) were used.

(1) Gastrin Receptor Antagonism

Preparation of gastric glands:

Male Hartley guinea pigs (450–600 g) were killed by bleeding and stomach was extracted from each animal immediately, from which gastric glands were prepared.

Preparation of test compounds and procedures of displacing assay

A 1M solution of a compound to be tested in DMSO is prepared and diluted with 50% DMSO to obtain a ten-fold dilution series.

The reaction is initiated by the addition of gastric glands to solutions of different concentration each containing $^{125}$I-labeled gastrin (final concentration, 0.2 nM). The mixture is incubated for 30 min at 25° C., centrifuged at 2000 rpm for 5 min and the supernatant is removed by aspiration. To the pellet is added ice-cooled incubation buffer and mixed gently, followed by an immediate centrifugation and removal of the supernatant by aspiration. The radioactivity is counted on gamma counter. The same procedure was repeated using 50% DMSO solution or human gastrin I (final concentration, 2 μM) instead of a solution of test compound so as to obtain the control value regarding total binding or the value regarding non-specific binding, respectively.

Calculation of IC$_{50}$:

The IC$_{50}$ was determined by plotting the ratio (%) of specific binding of a test compound to that of control on semilogarithmic graph and obtaining the concentration corresponding to 50%, wherein:

specific binding of control=total binding (cpm)–non-specific binding (cpm); and specific binding of test compound=total binding (cpm)–non-specific binding (cpm).

(2) CCK-A Receptor Antagonism and CCK-B Receptor Antagonism

Preparation of CCK receptor preparations

Male ddY mice (24 to 30 g) were killed by decapitation and cerebral cortex (CCK-B) and pancreas (CCK-A) were extracted immediately. Each of cerebral cortex and pancreas was mixed with 50 mM Tris-HCl buffer (pH 7.4) and homogenized with a teflon-glass homogenizer and polytron homogenizer to obtain crude membrane specimens.

Preparation of test compounds and procedures of displacing assay A 1M solution of a compound to be tested in DMSO is prepared and diluted with 50% DMSO to obtain a ten-fold dilution series.

The reaction is initiated by the addition of crude membrane specimen to solutions of different concentration each containing [$^3$H]CCk-8 (final concentration, 1 nM). The mixture is incubated for 90 min at 25° C., filtered through glass filter with aspiration and washed with a cooled 50 mM Tris buffer. After the addition of Aquazol-2 cocktail the radioactivity is counted. The same procedure was repeated using 50% DMSO solution or Ceruletide (final concentration, 1 μM) instead of a solution of test compound so as to obtain the control value regarding total binding or the value regarding non-specific binding, respectively.
Calculation of $IC_{50}$:

The $IC_{50}$ was determined by plotting the ratio (%) of specific binding of a test compound to that of control on semilogarithmic graph and obtaining the concentration corresponding to 50%, wherein:

specific binding of control=total binding (cpm)−non-specific binding (cpm); and specific binding of test compound=total binding (cpm)−non-specific binding (cpm).

Results are shown in Table 1 below.

TABLE 1

| Compound No. | Receptor | | | Inhibitory Effect on acid secretion |
|---|---|---|---|---|
| | Gastrin | CCK-B | CCK-A | (Schild method) |
| | ($IC_{50}$, nM) | | | (mg/kg):(%)* |
| 8a | 7 | 54 | 860 | 0.3:49 |
| 8d | 4 | 11 | 29 | 0.3:66 |
| 8f | 3 | 17 | 120 | 0.3:73 |
| 8h | 5 | 18 | 380 | 0.3:81 |
| 8o | 12 | 23 | 860 | 0.3:60 |
| 8r | 18 | 21 | 760 | 0.3:46 |
| 8s | 2 | 2 | 100 | |
| 9a | 8 | 130 | 2,100 | |
| 9b | 14 | 120 | 360 | |
| 9d | 6 | 11 | <100 | |
| 9f | 7 | 62 | 1,400 | |
| 9g | 3 | 7 | 420 | |
| 9h | 4 | 20 | 1,250 | |
| 9i | 7 | 2 | 290 | |
| 9o | 31 | 78 | 3,900 | |
| 10c | 64 | 380 | 2,100 | |
| 10s | 7 | 4 | <100 | |
| 11f | 6 | 38 | 800 | |
| 11o | 18 | 36 | 1,850 | |
| 17-i | 7 | 140 | 1,350 | 0.3:44 |
| 17-ii | 5 | 105 | >10,000 | 0.3:72 |
| 17-iii | 6 | 190 | 11,500 | 0.3:47 |
| 17-iv | 2 | 8 | 2,900 | 0.1:44 |
| 17-v | 16 | 180 | 3,600 | 0.3:59 |
| 17-vi | 3 | 16 | 4,400 | 0.3:22 |
| 17-vii | 11 | 4 | 1,800 | 0.3:68 |
| 17-viii | 2 | 6 | 460 | 0.3:76 |
| 17-ix | 0.6 | 2 | 500 | 0.1:74 |
| 17-x | 1 | 3 | 360 | 0.3:70 |
| 17-xi | 6 | 115 | >10,000 | 0.3:39 |
| 17-xii | 15 | 48 | 2,500 | 0.3:48 |
| 17-xiii | 2 | 7 | 4,800 | 0.3:21 |
| 17-xvii | <1 | 1 | 1,300 | 0.1:30 |
| 18-i | 25 | 440 | 3,200 | |
| 18-iv | 4 | 38 | 3,600 | 0.3:65 |
| 18-xiii | 7 | 29 | 10,500 | 0.3:26 |
| 19-iv | 6 | 26 | 2,600 | 0.5:58 |
| 20-iv | 2 | 3 | 380 | 0.3:65 |

Experiment 3

In Vitro Test for Evaluation of Histamine $H_2$ Receptor Antaqonism

The Histamine $H_2$ receptor antagonism was evaluated by determining $PA_2$ in the following manner.

Male Hartley guinea pigs (450 to 600 g) were killed by bleeding and right atrium was extracted from each animal and suspended in Magnus device (Krebs bicarbonate buffer aerated with 95% $O_2$ and 5% $CO_2$ at 30° C.). To the device was added histamine cumulatively and the time-course effect of histamine was evaluated.

The $pA_2$ values which are the parameter reflecting the activity of histamine $H_2$ antagonism were calculated as a negative logarithm of a concentration of an antagonist required to shift the dose-response curve of histamine so that the concentration is doubled. [TAKAYANAGI K., IYAKUHIN-KAIHATSU KISO-KOZA V. (TSUDA K., NOGAMI, T. Ed.), Chijin-Kan, p. 731–776, Tokyo (1974); and Van Rossum, J. M., Arch. Int. Pharmacodyn. Ther., 143: 299–330 (1963)]

Experiment 4

Effect of Gastrin Receptor in the Prevention of Relapse of Ulcer Followinq the Administration of $H_2B$ The usefulness of benzodiazepine derivatives prepared in Examples in the anti-ulcer treatment was evaluated in the following experiments. Thus, the effect of combined formulation of a histamine $H_2$ receptor antagonist ($H_2B$) and a known gastrin receptor antagonist in the relief or prevention of the relapse of ulcer following the continuous administration of $H_2B$ was evaluated. In the experiment, the evaluation of the inhibitory effect of gastrin receptor antagonist was conducted after an interruption of few days following a continuous administration of $H_2B$ which is thought to be the cause of relapse of ulcer using as criterion, (1) increase in gastric acid secretion (rebound effect); and (2) the decrease in the protecting function of gastric mucosa.

Materials

Male Sprague Dawley rats weighing from 240 to 280 g were used as experimental animals.

As $H_2B$, famotidine, and as gastrin receptor antagonist, L-365,260 described in Example 281 of Japanese Patent Publication (KOKAI) 63-238069 (EP 167,919; EP 284,256; U.S. Pat. No. 4,820,834; U.S. Pat. No. 5,004,741)), were used. A combined formulation was prepared by mixing famotidine (M.W., 337.4) and L-365,260 (M.W., 398.44) in the ratio of 1:1 because these substances have almost the same molecular weight. For administration, a suspension of 10 mg famotidine or L-365,260 in 1 ml vehicle (0.5% methyl cellulose solution) was prepared. The combined formulation is a mixture of an equal amount of each suspension.

Administration Procedure

A previously determined dose of each test compound (1.0 ml or 3.0 ml/kg) was charged in a syringe and administered orally to a rat directly into gaster using a stainless probe needle (φ1.2×L 80 mm) equipped to the syringe.

Experimental Procedure

A. Single administration test (1) Gastric damage due to stress induced by restricted water-immersion (single administration test)

Twenty four hour starved (ad libitum for water) male Sprague Dawley rats (270–290 g) were orally administered with a test compound and, 30 min later, were loaded with stress in the following manner. Rats were placed in a stress cage (Natsume Seisakusyo) and immersed in water tank at 23° C. upto the level of pectoral processus xiphoideus [Takagi et al, Chem. Pharm. Bull (Tokyo) 12, 465–472 (1964)]. Seven hours later, animals were withdrawn from the water tank and killed with ether. The gaster was extracted and 1% formalin solution (13 ml) was injected in it. The gaster was fixed by dipping in 1% formalin solution for 10 min, cut out along the greater curvature and developed on a glass plate (hereinafter, referred to as formalin treatment). The gaster was observed under anatomic microscope (x10) and longer diameter (mm) of each damages (bleeding erosion) appearing around fundic glands was measured.

B. Continuous administration test (A) A group consists of animals that received vehicle (0.5% methyl cellulose solution, 1 ml/kg).

(B) A group consists of animals that received famotidine (a suspension of 10 mg famotidine in 1 ml 0.5% methyl cellulose) continuously at a dose of 10 or 30 mg/kg/day.

(C) A group consists of animals that received L-365,260 continuously at a dose of 10 mg/kg/day.

(D) A group consists of animals that received a combined formulation of famotidine and L-365,260 at a dose of 10 mg/kg/day for each compound.

(2) Basic gastric acid secretion after interruption following the continuous administration of famotidine To a rat bred normally was administered continuously famotidine at a dose of 10 or 30 mg/kg/day for a week. After the final administration, the basis gastric acid secretion (total acid excretion) was determined according to the pylorus ligation method (4-hour-method) [Shay, H. et al., Gastroenterology, 5: 43–61 (1945)]. The determination was carried out following the final administration, immediately, 24 and 48 hr (2 days) later, in the case of the group regarding continuous administration of 10 mg/kg/day, and immediately, 3 and 4 days later, in the case of the group regarding continuous administration of 30 mg/kg/day.

Thus, rats were subjected to laparotomy under ether anesthetization and pylorus was ligated. Four hours later, gaster was extracted under ether anaesthetization and the accumulated gastric juice was collected. After centrifugation (3000 rpm, 10 min), pH and acidity of gastric juice was determined. The acidity was measured upto pH 7.0 with 0.1N NaOH. The total acid secretion (µEq/4 hr) was calculated by multiplying acidity by the volume of juice for each animal.

(3) Aspirin-induced gastric mucosa damage following a continuous administration of famotidine After two-day-interruption following a continuous administration of famotidine, aspirin (200 mg/kg) was administered to rats orally. Seven hours later, gaster was extracted under ether anesthetization and subjected to formalin treatment with 1% formalin solution. The length (mm) of gastric mucosa damage appearing around fundic glands was then measured. Lesion index was calculated by adding all the measurements. Rats had been starved for 24 hr before aspirin administration (ad libitum for water).

Experimental Results (1) Gastric damage due to stress induced by restricted water-immersion Results are shown in Table 2 below.

TABLE 2

Effect of famotidine, L-365, 260 and famotidine + L365, 260 on gastric damage due to stress induced by restricted water-immersion in rats

| Treatment | dose (mg/kg) | administration route | rat number | lesion index (% to control) |
|---|---|---|---|---|
| Control (0.5% M.C.) | | p.o.** | 10 | 100 ± 8.1 |
| Famotidine | 1 | p.o. | 10 | 33.4 ± 5.5* |
| L-365, 260 | 1 | p.o. | 10 | 130.4 ± 20.6 |
| Famotidine + | 1 + 1 | p.o. | 10 | 37.8 ± 10.2* |

TABLE 2-continued

Effect of famotidine, L-365, 260 and famotidine + L365, 260 on gastric damage due to stress induced by restricted water-immersion in rats

| Treatment | dose (mg/kg) | administration route | rat number | lesion index (% to control) |
|---|---|---|---|---|
| L-365, 260 | | | | |
| Control (0.5% M.C.) | | p.o. | 10 | 100 ± 14.7 |
| Famotidine | 3 | p.o. | 10 | 33.4 ± 5.5* |
| L-365, 260 | 3 | p.o. | 10 | 84.7 ± 17.4 |
| Famotidine + L-365, 260 | 3 + 3 | p.o. | 10 | 28.2 ± 6.9* |

*p < 0.05 (compared with each control)
**p.o. = oral administration

L-365,260 does not inhibit the appearance of stress gastric damage at either dose (1 or 3 mg/kg). Famotidine inhibited the appearance significantly at a dosage of 3 mg/kg. The group related to a combined formulation showed stronger inhibition compared to a single formulation at any dosage. (see, Table 2)

(2) Basic gastric acid secretion after interruption following the continuous administration of famotidine

TABLE 3

Gastric acid excretion immediately after the continuous administration (7 days) of famotidine in rats with pylorus ligation

| Treatment | dose (mg/kg/day) | rat number | total acid secretion (µEg/49 hr) | inhibition (%) |
|---|---|---|---|---|
| Control (0.5% M.C.) | | 5 | 395.4 ± 41.9 | |
| Famotidine | 10 | 5 | 151.8 ± 29.8** | 61.6 |
| | 30 | 5 | 158.4 ± 54.9** | 59.9 |

**P < 0.01 (compared with each control)

TABLE 4

Gastric acid excretion at 24 and 48 hours after the continuous administration (7 days) of famotidine in rats with pylorus ligation

| Hr** | Treatment | dose (mg/kg/day) | rat number | total acid secretion (µEq/4 hr) | in- hibition (%) |
|---|---|---|---|---|---|
| 24 | Control (0.5% M.C.) | | 4 | 593.7 ± 129.9 | |
| | Famotidine | 10 | 4 | 821.0 ± 214.2 | −38.3 |
| 48 | Control (0.5% M.C.) | | 4 | 461.2 ± 56.6 | |
| | Famotidine | 10 | 4 | 948.9 ± 187.5* | −105.7 |

*P < 0.5 (compared with each control)
**After treatment.

TABLE 5

Gastric acid excretion on 3 and 4 days after the continuous administration (7 days) of famotidine in rats with pylorus ligation

| Day** | Treatment | dose (mg/kg/day) | rat number | total acid secretion (μEq/4 hr) | in- hibition (%) |
|---|---|---|---|---|---|
| 3 | Control (0.5% M.C.) | | 11 | 585.8 ± 94.2 | |
| | Famotidine | 30 | 8 | 850.9.0 ± 176.2 | −45.3 |
| 4 | Control (0.5% M.C.) | | 10 | 473.3 ± 61.2 | |
| | Famotidine | 30 | 10 | 682.5.9 ± 65.3* | −44.2 |

*P < 0.5 (compared with each control)
**After treatment.

In the group that received famotidine (10 mg/kg/day) continuously, the basic gastric acid secretion was inhibited significantly ($P<0.05$) immediately after interrupting the administration though, it increased significantly ($P<0.05$) after a 48-hour-interruption. In the group that received famotidine (30 mg/kg/day) continuously, the basic gastric acid secretion was inhibited significantly ($P<0.05$) immediately after interrupting the administration though, it increased significantly ($P<0.05$) after a 4-day-interruption. (see, Tables 3, 4 and 5)

TABLE 6

Gastric acid excretion on 2 and 3 days after the continuous administration (7 days) of famotidine, L-365, 260 and famotidine + L-365, 260

| Day** | Treatment | dose (mg/kg/day) | rat number | total acid secretion (μEq/4 hr) |
|---|---|---|---|---|
| 2 | Control (0.5% M.C.) | | 5 | 609.5 ± 60.5 |
| | Famotidine | 10 | 5 | 788.4 ± 217.7 |
| | L-365, 260 | 10 | 4 | 631.4 ± 147.9 |
| | Famotidine + L-365, 260 | 10 + 10 | 5 | 559.0 ± 66.7 |
| 3 | Control (0.5% M.C.) | | 4 | 355.8 ± 49.9 |
| | Famotidine | 10 | 5 | 682.4 ± 132.6 |
| | L-365, 260 | 10 | 4 | 681.0 ± 142.9 |
| | Famotidine + L-365, 260 | 10 + 10 | 5 | 494.8 ± 130.5 |

**After treatment.

With respect to plasma gastrin concentration, it increased significantly ($P<0.05$) immediately after the continuous administration, reflecting the inhibition of acid excretion compared with control though, only little difference could be observed between the treated group and control group on 1 to 3 days after interruption of administration.

The increase in the acid excretion after interruption following the continuous administration of famotidine (10 mg/kg/day) had a tendency to be inhibited by combining famotidine (10 mg/kg) with L-365,260 (10 mg/kg).

In the group that received a continuous administration of L-365,260 alone for a week, the results did not differed from those obtained in control group. (see, Table 6)

(3) Aspirin-induced gastric mucosa damage following a continuous administration of famotidine

TABLE 7

Effect of a continuous administration (7 days) of famotidine, L-365, 260 and famotidine + L-365, 260 on aspirin-induced gastric mucosa damage

| Treatment | dose (mg/kg) | administration route | rat number | lesion index (mm²) |
|---|---|---|---|---|
| Control | | p.o. | 5 | 20.8 ± 4.0 |
| Famotidine | 10 | p.o. | 5 | 67.0 ± 14.2* |
| L-365, 260 | 10 | p.o. | 5 | 43.2 ± 13.7 |
| Famotidine + L-365, 260 | 10 + 10 | p.o. | 5 | 27.2 ± 12.2 |

Note: Aspirin (200 mg/kg) was administered orally to a rat after two-day-interruption following each continuous administration.
*P < 0.01 (compared with each control)

Many linear-shaped damages caused by aspirin appeared at the gastric body.

As is apparent from the table above, in the group that received a continuous administration of famotidine, the condition deteriorated significantly ($P<0.05$) compared with control group, while in the group that received a combined formulation of famotidine and L-365,260, the deterioration was inhibited significantly ($P<0.05$). In the group that received L-365,260 continuously, the condition seemed to have tendency to deteriorate, but it is not significant.

An increase in the basic acid secretion (acid rebound) was observed on the 2nd day after interruption following the continuous administration of famotidine. It is considered to be a phenomenon common to $H_2B$. The gastric mucosa reactivity in the group that received continuous administration of famotidine was tested, which revealed that the ulcer index got worse significantly on the 2nd day after interruption. This result is in good agreement with the point where the acid rebound was observed as mentioned above. These facts indicate that famotidine treatment weakens the protective function of gastric mucosa.

It was proved that the reverse effect of famotidine, that is, acid rebound phenomenon and deterioration of aspirin-induced gastric mucosa damage, can be inhibited by using famotidine in combination with L-365,260. These results generally show that the appearance of gastric damages following the treatment of ulcer with $H_2B$ can be prevented by combining it with a gastrin receptor antagonist (see, Table 7).

Experimental results shown above demonstrate that the benzodiazepine derivatives of the present invention have antagonistic effect against gastrin receptor and CCK-B receptor, and that a hybrid-type compound consisting of a compound of the present invention and an $H_2B$ is inhibitory against the acid-rebound phenomenon and decrease in the protective function of gastric mucosa following anti-ulcer treatment, and is useful as an anti-ulcer agent unaccompanied by relapse.

The method of preparing pharmaceutical compositions of the present invention is shown below, which is provided only for illustrative purpose.

| | |
|---|---|
| Compound 17ix | 50.0 mg |
| Lactose | 128.0 mg |
| Potato starch | 40.0 mg |
| Magnesium stearate | 2.0 mg |
| | 220.0 mg |

A 10% viscous solution of potato starch was prepared by heating. Compound 17ix, lactose and the rest of potato starch were mixed with the resultant viscous solution and granulated by passing through a sieve (mesh size 1.5 mm). The granules were dried at 45° C., passed through the same sieve again, mixed with magnesium stearate and formulated with tabletting machine.

| Compound 17ix | 200.0 mg |
|---|---|
| Lactose | 120.0 mg |
| Corn starch | 70.0 mg |
| Polyvinylpyrrolidone | 8.0 mg |
| Magnesium stearate | 2.0 mg |
| | 400.0 mg |

Compound 17ix, lactose and corn starch were moistured homogeneously with aqueous polyvinylpyrrolidone solution and granulated by passing through a sieve (mesh size 2.0 mm). The granules were dried at 50° C. with circulating air system, re-granulated by passing through a sieve (mesh size 1.5 mm), mixed with magnesium stearate, and formulated with tabletting machine.

Formulation 3 Capsules

Compound 17ix (60.0 mg) was pulverized to fine powder and filled into capsules to give capsule formulation.

Formulation 4 Suppository

| Compound 17ix | 60.0 mg |
|---|---|
| Suppository base | 1640.0 mg |
| | 1700.0 mg |

Finely pulverized Compound 17ix was suspended into melted suppository base. The resultant suspension was cooled to 40° C. and poured into a slightly cooled suppository mold at 37° C.

Formulation 5 Suppository

| Compound 17ix | 200.0 mg |
|---|---|
| Suppository base | 1500.0 mg |
| | 1700.0 mg |

The suppository base was melted. An active ingredient pulverized at 38° C. was dispersed into the melted base homogeneously. The dispersion was cooled to 35° C. and poured into previously cooled suppository mold.

Formulation 6 Suspension

| Compound 17ix | 4.0 g |
|---|---|
| Carboxymethyl cellulose | 0.1 g |
| Methyl p-hydroxybenzoate | 0.05 g |
| Propyl p-hydroxybenzoate | 0.01 g |
| Sucrose | 10.0 g |
| Glycerin | 5.0 g |
| 70% Sorbitol solution | 20.0 g |
| Fragrance | 0.3 g |
| Distilled water | |
| | 1000 ml |

Distilled water was warmed at 70° C.and methyl p-hydroxybenzoate, propyl p-hydroxybenzoate, glycerin and carboxymethyl cellulose are dissolved therein. The resultant solution was cooled to room temperature. Compound 17ix was added dropwise to the solution with stirring and dispersed homogeneously. Sucrose, sorbitol and fragrance were added and dissolved. The resultant suspension was subjected to deaeration under vacuum with stirring.

What is claimed is:

1. A compound of the formula (I):

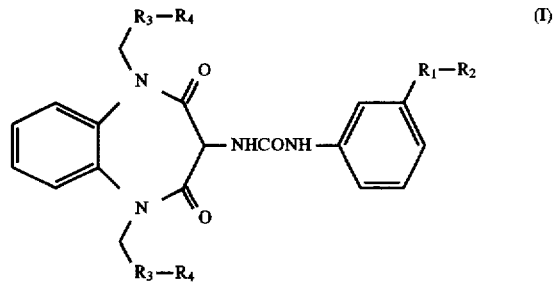

wherein $R_1$ is a bond, $-CH_2-$, $-CH_2O-$, $-OCH_2-$, $-SCH_2-$ or a group of the formula:

$R_2$ is a lower alkyl, $-COOR_5$, $-CONH(CH_2)_nCOOR_5$, $-CONHSO_2R_5$, $-SO_2NHCOR_5$, or a heterocyclic group selected from the group consisting of furyl, thienyl, tetrazolyl, pyrrolyl, pyrazolyl, imidazolyl, oxazolyl, thiazolyl pyridinyl, oxadinyl, triazinyl, pyrrolidinyl, thiazolidinyl, oxazolidinyl imidazolidinyl, thiazolinyl, oxazolinyl, imidazolinyl, piperidinyl, piperadinyl, morpholinyl, thiomorpholinyl, oxadiazolyl and dioxanyl, which is unsubstituted or substituted with one or more substituents selected from the group consisting of hydroxy, carbonyl, amino, amino protected with an amino-protecting group, halogen, lower alkyl and lower alkoxy ($R_5$ is a hydrogen atom, lower alkyl or benzyl and n is an integer of 1 to 5); $R_3$ is a bond, $-CO-$ or $-CONH-$; and $R_4$ is a heterocyclic group selected from the group consisting of furyl, thienyl, tetrazolyl, pyrrolyl, pyrazolyl, imidazolyl, oxazolyl, thiazolyl, pyridinyl, oxadinyl, triazinyl, pyrrolidinyl, thiazolidinyl, oxazolidinyl, imidazolidinyl, thiazolinyl, oxazolinyl, imidazolinyl, piperidinyl, piperadinyl, morpholinyl, thiomorpholinyl, oxadiazolyl and dioxanyl, which is unsubstituted or substituted with one or more substituents selected from the group consisting of hydroxy, carbonyl, amino, amino protected with an amino-protecting group, halogen, lower alkyl and lower alkoxy, lower alkyl which is unsubstituted or substituted with one or more substituents selected from the group consisting of hydroxy, carbonyl, amino, amino protected with an amino-protecting group, halogen, lower alkyl and lower alkoxy, lower cycloalkyl, which is unsubstituted or substituted with one or more substituents selected from the group consisting of hydroxy, carbonyl, amino, amino protected with an amino-protecting group, halogen, lower alkyl and lower alkoxy, aryl selected from the group consisting of phenyl and naphthyl which is unsubstituted or substituted with one or more substituents selected from the group consisting of hydroxy, carbonyl, amino, amino protected with an amino-protecting group, halogen, lower alkyl and lower alkoxy, a lower alkoxycarbonyl group, or a pharmaceutically acceptable salt thereof, and wherein $R_3$ is the same at each instance in said compound, and wherein $R_4$ is the same at each instance in said compound.

2. The compound of the formula (I) of claim 1, wherein $R_3$ is —CO— and $R_4$ is a lower cycloalkyl group.

3. The compound of claim 1 or 2, wherein $R_1$-$R_2$ is —$COOR_5$, —$CONHSO_2R_5$, —$SO_2NHCOR_5$, —$CH_2COOR_5$, —$OCH_2COOR_5$, -$SCH_2COOR_5$, tetrazolylmethyloxy or a 5-membered heterocyclic group containing a N atom.

4. A compound of the formula (III):

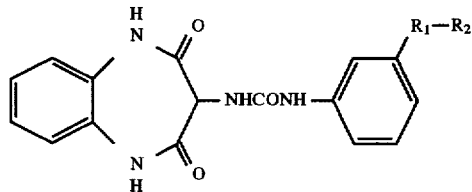

wherein $R_1$ is a bond, —$CH_2$—, —$CH_2O$—, —$OCH_2$—, —$SCH_2$— or a group of the formula:

and $R_2$ is a lower alkyl, —$COOR_5$, —$CONH(CH_2).COOR_5$, —$CONHSO_2R_5$, —$SO_2NHCOR_5$, or a heterocyclic group selected from the group consisting of furyl, thienyl, tetrazolyl, pyrrolyl, pyrazolyl, imidazolyl, oxazolyl, thiazolyl, pyridinyl, oxadinyl, triazinyl, pyrrolidinyl, thiazolidinyl, oxazolidinyl, imidazolidinyl thiazolinyl, oxazolinyl, imidazolinyl, piperidinyl, piperadinyl, morpholinyl, thiomorpholinyl, oxadiazolyl and dioxanyl, which is unsubstituted or substituted with one or more substituents selected from the group consisting of hydroxy, carbonyl, amino, amino protected with an amino-protecting group, halogen, lower alkyl and lower alkoxy ($R_5$ is a hydrogen atom, lower alkyl or benzyl and n is an integer of 1 to 5).

5. A pharmaceutical composition comprising a therapeutically effective amount of at least one compound of claim 1 and at least one pharmaceutically acceptable carrier therefor.

* * * * *